United States Patent
Volgraf et al.

(10) Patent No.: US 10,280,165 B2
(45) Date of Patent: May 7, 2019

(54) PYRIDOPYRIMIDINONES AND METHODS OF USE THEREOF

(71) Applicant: Genentech, Inc., South San Francisco, CA (US)

(72) Inventors: Matthew Volgraf, Oakland, CA (US); Yu Jiang, Beijing (CN); Elisia Villemure, San Francisco, CA (US); Benjamin Sellers, Larkspur, CA (US); Guosheng Wu, Beijing (CN); Aijun Lu, Beijing (CN)

(73) Assignee: Genentech, Inc., South San Francisco, CA (US)

( * ) Notice: Subject to any disclaimer, the term of this patent is extended or adjusted under 35 U.S.C. 154(b) by 0 days.

(21) Appl. No.: 15/783,373

(22) Filed: Oct. 13, 2017

(65) Prior Publication Data
US 2018/0127414 A1 May 10, 2018

Related U.S. Application Data

(63) Continuation of application No. PCT/EP2016/057962, filed on Apr. 12, 2016.

(30) Foreign Application Priority Data
Apr. 15, 2015 (WO) ................ PCT/CN2015/076617

(51) Int. Cl.
*A61K 31/519* (2006.01)
*C07D 471/04* (2006.01)
*A61P 25/00* (2006.01)

(52) U.S. Cl.
CPC ............ *C07D 471/04* (2013.01); *A61P 25/00* (2018.01)

(58) Field of Classification Search
CPC .......................... A61K 31/519; C07D 471/04
USPC ..................... 514/259.41; 544/282
See application file for complete search history.

(56) References Cited

U.S. PATENT DOCUMENTS

2007/0155779 A1  5/2007  Verhoest et al.
2016/0222033 A1  4/2016  Yu et al.

FOREIGN PATENT DOCUMENTS

WO  2004/074270 A2  9/2004
WO  2014/202493 A1  12/2014
WO  2016/166078     10/2016

OTHER PUBLICATIONS

Agamennone et al., "Identification of small molecules acting against H1N1 influenza A virus" Virology 488:249-258 (Dec. 3, 2015).
Costa et al., "A Novel Family of Negative and Positive Allosteric Modulators of NMDA Receptors" Journal of Pharmacology and Experimental Therapeutics 335(3):614-621 (Dec. 1, 2010).
Ferrarini et al., "Study on Affinity Profile toward Native Human and Bovine Adenosine Receptors of a Series of 1,8-Naphthyridine Derivatives" Journal of Medicinal Chemistry 47(12):3019-3031 (Jan. 1, 2004).
Guo Chuangxing et al., "Discovery of 2-((1H-benzo[d]imidazol-1-yl)methyl)-4H-pyrido[1,2-a]pyrimidin-4-ones as novel PKM2 activators" Bioorganic & Medicinal Chemistry Letters 23(11):3358-3363 (Apr. 1, 2013).
Hackos et al., "Positive Allosteric Modulators of GluN2A-Containing NMDARs with Distinct Modes of Action and Impacts on Circuit Function" Neuron 89:983-999 ( 2016).
Kennis et al., "New substituted 1,2,3,4-tetrahydrobenzofuro[3,2-c]pyridine having highly active and potent central a2-antagonistic activity as potential antidepressants" Bioorganic & Medicinal Chemistry Letters 10:71-74 (Jan. 1, 2000).
Molnár et al., "Suzuki-Miyaura cross-coupling reactions of halo derivatives of 4H-pyrido[1,2-a]pyrimidin-4-ones" Organic & Biomolecular Chemistry 9(19):6559 (Jan. 1, 2011).
Villemure et al., "GluN2A-Selective Pyridopyrimidinone Series of NMDAR Positive Allosteric Modulators with an Improved in Vivo Profile" ACS Medicinal Chemistry Letters 8:84-89 ( 2017).
Volgraf et al., "Discovery of GluN2A-Selective NMDA Receptor Positive Allosteric Modulators (PAMs): Tuning Deactivation Kinetics via Structure-Based Design" Journal of Medicinal Chemistry 59:2760-2779 ( 2016).

*Primary Examiner* — Jeffrey H Murray
(74) *Attorney, Agent, or Firm* — Brian L. Buckwater

(57) ABSTRACT

The invention relates to pyridopyrimidinone compounds of formula I

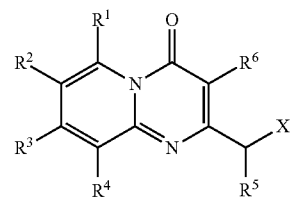

or pharmaceutically acceptable salts thereof, wherein X, $R^1$, $R^2$, $R^3$, $R^4$, $R^5$ and $R^6$ are as defined herein, as well as pharmaceutical compositions comprising such compounds, and methods of treatment using such compounds.

28 Claims, No Drawings

PYRIDOPYRIMIDINONES AND METHODS OF USE THEREOF

RELATED APPLICATIONS

This application is a continuation of International Application No. PCT/EP2016/057962, filed Apr. 12, 2016, claiming priority to application number PCT/CN2015/076617 filed Apr. 4, 2015, each of which are incorporated herein by reference in its entirety.

FIELD OF THE INVENTION

The present invention relates to certain pyridopyrimidinone compounds, pharmaceutical compositions comprising such compounds, and methods of treating neurological and psychiatric conditions, and other diseases and medical conditions, with such compounds and pharmaceutical compositions. The present invention also relates to certain pyridopyrimidinone compounds for use in modulating NMDA receptor activity.

BACKGROUND OF THE INVENTION

N-Methyl-D-aspartate (NMDA) receptors play an important role in various central nervous system functions, such as synaptic transmission and synaptic plasticity, and underlying functions such as regulation of long-term potentiation, long-term depression, and experience, dependent synaptic refinement. Costa et al., "A Novel Family of Negative and Positive Allosteric Modulators of NMDA Receptors," *J. Pharmacol. Exp. Ther.* 2010, 335, 614-621, at 614. Excitatory nerve transmission in these receptors is regulated by the neurotransmitter, L-glutamate, and the agonist, NMDA. PCT Intl. Publ. No. WO2007/006175, paras. 2-3. NMDA receptors are ligand-gated ion channels comprising seven subunits: GluN1, GluN2A-D, and GluN3A-B. Costa at 615. The NR2A and NR2B subunits have been implicated in glutamate binding to the receptor, while the NR1 subunit may play a role in the binding of the receptor co-agonist, glycine. The three-dimensional structures of the glutamate- and glycine-binding pockets of NMDA receptors have been characterized, allowing for design of more subtype-specific modulators.

Modulation of these receptors effects changes in learning and memory, and modulators of NMDA receptor activity are considered as potential treatments for neurological and psychiatric conditions including pain, neuropathic pain, inflammatory pain, peripheral neuropathy, stroke, epilepsy, neurodegeneration, schizophrenia, drug addiction, mood disorders, post-traumatic stress disorder, seizures, convulsions, age-associated memory impairment, and depression. Costa at 614. Modulation of NMDA receptor activity is linked with a neuroprotective role, with applications in treatments for stroke, traumatic brain injury, ischemia, and neurodegenerative diseases such as Alzheimer's disease, Parkinson's disease, Huntington's disease, amyotrophic lateral sclerosis, and Creutzfeldt-Jakob disease. Costa at 614-615.

There is a particular need for NMDA receptor modulators that demonstrate subtype selectivity among members of the NMDA receptor family. Selective agents will allow for optimal therapeutic activity with a reduced potential for adverse side effects. Costa at 615.

There remains a need for potent NMDA receptor modulators with desirable pharmaceutical properties.

SUMMARY OF THE INVENTION

The invention provides compounds of formula I

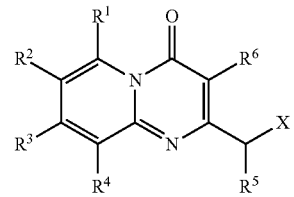

or pharmaceutically acceptable salts thereof, wherein:
X is:
  —O—Ar;
  —NR$^a$—Ar; or
  —Ar;
R$^1$ is:
  hydrogen;
  C$_{1-6}$alkyl;
  halo;
  C$_{1-6}$alkoxy;
  cyano;
  heteroaryl selected from furanyl, thienyl, pyrrolyl, pyrazolyl, imidazolyl, pyridinyl and pyrimidinyl, each of which may be unsubstituted or substituted once or twice with R$^b$;
  —C(O)—NHR$^c$;
  —C(O)—R$^c$; or
  cyclopropyl which may be unsubstituted or substituted once or twice with R$^d$;
R$^2$ is:
  hydrogen;
  C$_{1-6}$alkyl;
  C$_{1-6}$alkoxy;
  halo; or
  halo-C$_{1-6}$alkyl;
R$^3$ is:
  hydrogen;
  C$_{1-6}$alkyl;
  C$_{1-6}$alkoxy;
  halo; or
  halo-C$_{1-6}$alkyl;
R$^4$ is:
  hydrogen; or
  C$_{1-6}$alkyl;
R$^5$ is:
  hydrogen; or
  C$_{1-6}$alkyl; and
R$^6$ is:
  hydrogen;
  C$_{1-6}$alkyl;
Ar is: phenyl or heteroaryl selected from furanyl, thienyl, pyrrolyl, pyrazolyl, imidazolyl, benzimidazolyl, pyridinyl and pyrimidinyl, wherein the phenyl or heteroaryl may be unsubstituted or substituted one, two or three times with R$^e$;
R$^a$ is:
  hydrogen; or
  C$_{1-6}$alkyl;
R$^b$ is:
  C$_{1-6}$alkyl;
  halo;
  halo-C$_{1-6}$alkyl; or
  cyclopropyl;

$R^c$ is:
  $C_{1-6}$alkyl; or
  halo-$C_{1-6}$alkyl;
each $R^d$ independently is:
  $C_{1-6}$alkyl;
  halo;
  halo-$C_{1-6}$alkyl;
  hydroxy-$C_{1-6}$alkyl;
  $C_{1-6}$alkoxy-$C_{1-6}$alkyl; or
  cyano;
each $R^e$ independently is:
  $C_{1-6}$alkyl;
  halo;
  halo-$C_{1-6}$alkyl;
  —NH—C(O)—$R^f$;
  cyano; or
  cyclopropyl; and
$R^f$ is furanyl, thienyl, pyrrolyl, pyrazolyl or imidazolyl.

Also provided are methods of making the compounds and using the compounds as positive allosteric modulators of NR2A for treatment of diseases and conditions associated with the central nervous system.

DETAILED DESCRIPTION OF THE INVENTION

Most chemical names were generated using IUPAC nomenclature herein. Some chemical names were generated using different nomenclatures or alternative or commercial names known in the art. In the case of conflict between names and structures, the structures prevail.

General Definitions

As used above, and throughout this disclosure, the following terms, unless otherwise indicated, shall be understood to have the following meanings. If a definition is missing, the conventional definition as known to one skilled in the art controls. If a definition provided herein conflicts or is different from a definition provided in any cited publication, the definition provided herein controls.

As used herein, the terms "including," "containing," and "comprising" are used in their open, non-limiting sense.

As used herein, the singular forms "a," "an," and "the" include plural referents unless the context clearly dictates otherwise.

To provide a more concise description, some of the quantitative expressions given herein are not qualified with the term "about." It is understood that, whether the term "about" is used explicitly or not, every quantity given herein is meant to refer to the actual given value, and it is also meant to refer to the approximation to such given value that would reasonably be inferred based on the ordinary skill in the art, including equivalents and approximations due to the experimental and/or measurement conditions for such given value. Whenever a yield is given as a percentage, such yield refers to a mass of the entity for which the yield is given with respect to the maximum amount of the same entity that could be obtained under the particular stoichiometric conditions. Concentrations that are given as percentages refer to mass ratios, unless indicated differently.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, the preferred methods and materials are now described. All publications mentioned herein are incorporated herein by reference to disclose and describe the methods and/or materials in connection with which the publications are cited.

Except as otherwise noted, the methods and techniques of the present embodiments are generally performed according to conventional methods well known in the art and as described in various general and more specific references that are cited and discussed throughout the present specification. See, e.g., Loudon, Organic Chemistry, 4$^{th}$ edition, New York: Oxford University Press, 2002, pp. 360-361, 1084-1085; Smith and March, March's Advanced Organic Chemistry: Reactions, Mechanisms, and Structure, 5$^{th}$ edition, Wiley-Interscience, 2001.

Chemical Definitions

As used herein, "alkyl" refers to a saturated, straight- or branched-chain hydrocarbon group having from 1 to 10 carbon atoms. Representative alkyl groups include, but are not limited to, methyl, ethyl, n-propyl, isopropyl, 2-methyl-1-propyl, 2-methyl-2-propyl, 2-methyl-1-butyl, 3-methyl-1-butyl, 2-methyl-3-butyl, 2,2-dimethyl-1-propyl, 2-methyl-1-pentyl, 3-methyl-1-pentyl, 4-methyl-1-pentyl, 2-methyl-2-pentyl, 3-methyl-2-pentyl, 4-methyl-2-pentyl, 2,2-dimethyl-1-butyl, 3,3-dimethyl-1-butyl, 2-ethyl-1-butyl, butyl, isobutyl, t-butyl, n-pentyl, isopentyl, neopentyl, n-hexyl, and the like, and longer alkyl groups, such as heptyl, octyl, and the like. As used herein, "lower alkyl" means an alkyl having from 1 to 6 carbon atoms.

The term "alkenyl" refers to straight chain or branched hydrocarbyl groups having from 2 to 6 carbon atoms and preferably 2 to 4 carbon atoms and having at least 1 and preferably from 1 to 2 sites of double bond unsaturation. This term includes, by way of example, bi-vinyl, allyl, and but-3-en-1-yl. Included within this term are the cis and trans isomers or mixtures of these isomers.

The term "alkynyl" refers to straight or branched monovalent hydrocarbyl groups having from 2 to 6 carbon atoms and preferably 2 to 3 carbon atoms and having at least 1 and preferably from 1 to 2 sites of triple bond unsaturation. Examples of such alkynyl groups include acetylenyl (—C≡CH), and propargyl (—CH$_2$C≡CH).

The term "alkoxy" as used herein includes —O-(alkyl), wherein alkyl is defined above.

"Aryl" means a mono-, bi-, or tricyclic aromatic group, wherein all rings of the group are aromatic and all ring atoms are carbon atoms. For bi- or tricyclic systems, the individual aromatic rings are fused to one another. Examples of aryl groups are 6 and 10 membered aryls. Further examples of aryl groups include, but are not limited to, phenyl, naphthalene, and anthracene.

The term "cyano" as used herein means a substituent having a carbon atom joined to a nitrogen atom by a triple bond.

The term "deuterium" as used herein means a stable isotope of hydrogen having one proton and one neutron.

The term "halo" represents chloro, fluoro, bromo, or iodo. In some embodiments, halo is chloro, fluoro, or bromo. The term "halogen" as used herein refers to fluorine, chlorine, bromine, or iodine.

The term "haloalkyl" represents an alkyl group substituted with one, two, three, or more halogen atoms. Examples of haloalkyl groups include fluoromethyl, difluoromethyl, trifluoromethyl, fluoroethyl, trifluoroethyl, and trifluoropropyl.

The term "hydroxy" means an —OH group.

The term "oxo" means an =O group and may be attached to a carbon atom or a sulfur atom.

The term "N-oxide" refers to the oxidized form of a nitrogen atom.

As used herein, the term "cycloalkyl" refers to a saturated or partially saturated, monocyclic, fused polycyclic, bridged polycyclic, or spiro polycyclic carbocycle having from 3 to 15 carbon ring atoms. A non limiting category of cycloalkyl groups are saturated or partially saturated, monocyclic carbocycles having from 3 to 6 carbon atoms. Illustrative examples of cycloalkyl groups include, but are not limited to, the following moieties:

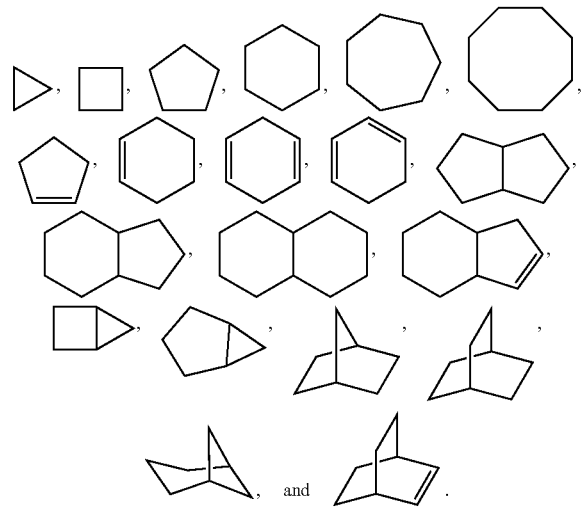

"Heterocycloalkyl" as used herein refers to a monocyclic, or fused, bridged, or spiro polycyclic ring structure that is saturated or partially saturated and has from three to 12 ring atoms selected from carbon atoms and up to three heteroatoms selected from nitrogen, oxygen, and sulfur. The ring structure may optionally contain up to two oxo groups on carbon or sulfur ring members, or an N-oxide. Illustrative heterocycloalkyl entities include, but are not limited to:

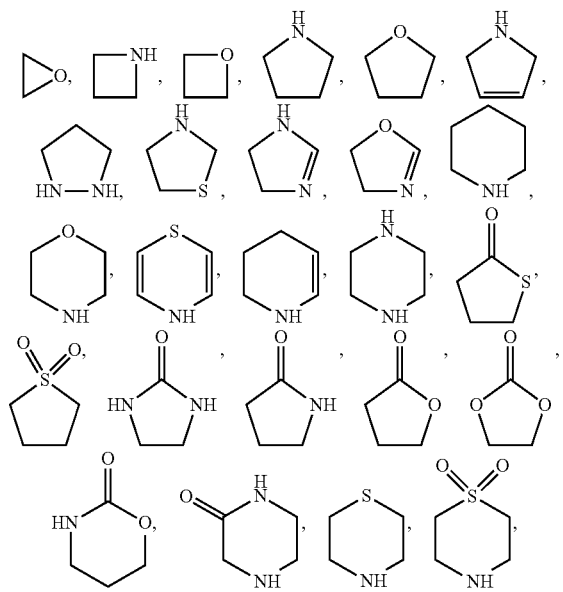

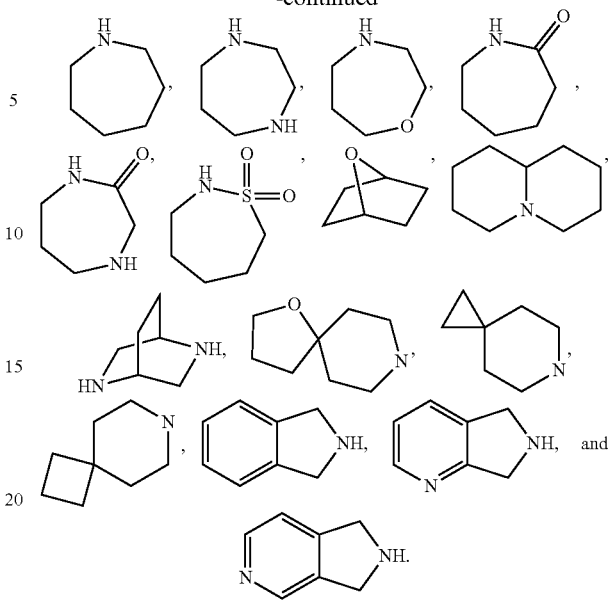

Heterocycloalkyl groups may be carbon-linked, meaning they are attached to the remainder of the molecule via a carbon atom, or nitrogen-linked, meaning they are attached to the remainder of the molecule via a nitrogen atom.

As used herein, the term "heteroaryl" refers to a monocyclic, or fused polycyclic, aromatic heterocycle having from three to 15 ring atoms that are selected from carbon, oxygen, nitrogen, and sulfur. Suitable heteroaryl groups do not include ring systems that must be charged to be aromatic, such as pyrylium. Suitable 5-membered heteroaryl rings (as a monocyclic heteroaryl or as part of a polycyclic heteroaryl) have one oxygen, sulfur, or nitrogen ring atom, or one nitrogen plus one oxygen or sulfur, or 2, 3, or 4 nitrogen ring atoms. Suitable 6-membered heteroaryl rings (as a monocyclic heteroaryl or as part of a polycyclic heteroaryl) have 1, 2, or 3 nitrogen ring atoms. Examples of heteroaryl groups include, but are not limited to, pyridinyl, imidazolyl, imidazopyridinyl, pyrimidinyl, pyrazolyl, triazolyl, pyrazinyl, tetrazolyl, furyl, thienyl, isoxazolyl, thiazolyl, oxazolyl, isothiazolyl, pyrrolyl, quinolinyl, isoquinolinyl, indolyl, benzimidazolyl, benzofuranyl, cinnolinyl, indazolyl, indolizinyl, phthalazinyl, pyridazinyl, triazinyl, isoindolyl, pteridinyl, purinyl, oxadiazolyl, triazolyl, thiadiazolyl, furazanyl, benzofurazanyl, benzothiophenyl, benzothiazolyl, benzoxazolyl, quinazolinyl, quinoxalinyl, naphthyridinyl, and furopyridinyl.

Those skilled in the art will recognize that the species of heteroaryl, cycloalkyl, and heterocycloalkyl groups listed or illustrated above are not exhaustive, and that additional species within the scope of these defined terms may also be selected.

As used herein, the term "substituted" means that the specified group or moiety bears one or more suitable substituents. As used herein, the term "unsubstituted" means that the specified group bears no substituents. As used herein, the term "optionally substituted" means that the specified group is unsubstituted or substituted by the specified number of substituents. Where the term "substituted" is used to describe a structural system, the substitution is meant to occur at any valency-allowed position on the system.

As used herein, the expression "one or more substituents" denotes one to maximum possible number of substitution(s)

that can occur at any valency-allowed position on the system. In a certain embodiment, one or more substituent means 1, 2, 3, 4, or 5 substituents. In another embodiment, one or more substituent means 1, 2, or 3 substituents.

Any atom that is represented herein with an unsatisfied valence is assumed to have the sufficient number of hydrogen atoms to satisfy the atom's valence.

When any variable (e.g., alkyl or $R^a$) appears in more than one place in any formula or description provided herein, the definition of that variable on each occurrence is independent of its definition at every other occurrence.

Numerical ranges, as used herein, are intended to include sequential whole numbers. For example, a range expressed as "from 0 to 4" or "0-4" includes 0, 1, 2, 3 and 4.

When a multifunctional moiety is shown, the point of attachment to the remainder of the formula can be at any point on the multifunctional moiety. In some embodiments, the point of attachment is indicated by a line or hyphen. For example, aryloxy- refers to a moiety in which an oxygen atom is the point of attachment to the core molecule while aryl is attached to the oxygen atom.

The nomenclature used herein to name the subject compounds is illustrated in the Examples herein. This nomenclature has generally been derived using the commercially-available LexiChem TK software (OpenEye, Santa Fe, N. Mex.).

Any formula given herein is intended to represent compounds having structures depicted by the structural formula as well as certain variations or forms. For example, compounds of any formula given herein may have asymmetric or chiral centers and therefore exist in different stereoisomeric forms. All stereoisomers, including optical isomers, enantiomers, and diastereomers, of the compounds of the general formula, and mixtures thereof, are considered to fall within the scope of the formula. Furthermore, certain structures may exist as geometric isomers (i.e., cis and trans isomers), as tautomers, or as atropisomers. All such isomeric forms, and mixtures thereof, are contemplated herein as part of the present invention. Thus, any formula given herein is intended to represent a racemate, one or more enantiomeric forms, one or more diastereomeric forms, one or more tautomeric or atropisomeric forms, and mixtures thereof.

The compounds described herein include pharmaceutically acceptable salt forms of compounds of Formula I or II. A "pharmaceutically acceptable salt" refers to a salt form of a free acid or base of a compound of Formula I or II that is non-toxic, is physiologically tolerable, is compatible with the pharmaceutical composition in which it is formulated, and is otherwise suitable for formulation and/or administration to a subject. Reference to a compound herein is understood to include reference to a pharmaceutically acceptable salt of said compound unless otherwise indicated.

Compound salts include acidic salts formed with inorganic and/or organic acids, as well as basic salts formed with inorganic and/or organic bases. In addition, where a given compound contains both a basic moiety, such as, but not limited to, a pyridine or imidazole, and an acidic moiety, such as, but not limited to, a carboxylic acid, one of skill in the art will recognize that the compound may exist as a zwitterion ("inner salt"); such salts are included within the term "salt" as used herein. Salts of the compounds of the invention may be prepared, for example, by reacting a compound with an amount of a suitable acid or base, such as an equivalent amount, in a medium such as one in which the salt precipitates or in an aqueous medium followed by lyophilization.

Exemplary acid addition salts include acetates, ascorbates, benzoates, benzenesulfonates, bisulfates, borates, butyrates, citrates, camphorates, camphorsulfonates, fumarates, hydrochlorides, hydrobromides, hydroiodides, isonicotinates, lactates, maleates, methanesulfonates, naphthalenesulfonates, nitrates, oxalates, phosphates, propionates, salicylates, succinates, sulfates, tartarates, thiocyanates, toluenesulfonates (also known as tosylates) and the like.

Exemplary basic salts include ammonium salts, alkali metal salts such as sodium, lithium, and potassium salts, alkaline earth metal salts such as calcium and magnesium salts, salts with organic bases (for example, organic amines) such as dicyclohexylamines, t-butyl amines, and salts with amino acids such as arginine, lysine and the like.

Additionally, acids and bases which are generally considered suitable for the formation of pharmaceutically useful salts from pharmaceutical compounds are discussed, for example, by P. Stahl et al., Camille G. (eds.) Handbook of Pharmaceutical Salts: Properties, Selection and Use. (2002) Zurich: Wiley-VCH; S. Berge et al., *J. Pharm. Sci.* (1977) 66(1) 1-19. These disclosures are incorporated herein by reference thereto.

Additionally, any compound described herein is intended to refer also to any unsolvated form, or a hydrate or solvate of such a compound, and mixtures thereof, even if such forms are not listed explicitly. "Solvate" means a physical association of a compound of the invention with one or more solvent molecules. This physical association involves varying degrees of ionic and covalent bonding, including hydrogen bonding. In certain instances the solvate will be capable of isolation, for example when one or more solvent molecules are incorporated in the crystal lattice of a crystalline solid. "Solvate" encompasses both solution-phase and isolatable solvates. Suitable solvates include those formed with pharmaceutically acceptable solvents such as water, ethanol, and the like. In some embodiments, the solvent is water and the solvates are hydrates. A compound of Formula I or II, including any hydrate or solvate forms, may be in the form of a crystalline polymorph, an amorphous solid, or a non-solid form.

The invention also relates to pharmaceutically acceptable prodrugs of the compounds of Formula I or II, and treatment methods employing such pharmaceutically acceptable prodrugs. The term "prodrug" means a precursor of a designated compound that, following administration to a subject, yields the compound in vivo via a chemical or physiological process such as solvolysis or enzymatic cleavage, or under physiological conditions (e.g., a prodrug on being brought to physiological pH is converted to the compound of Formula I or II). A "pharmaceutically acceptable prodrug" is a prodrug that is non-toxic, biologically tolerable, and otherwise suitable for formulation and/or administration to the subject. Illustrative procedures for the selection and preparation of suitable prodrug derivatives are described, for example, in "Design of Prodrugs", ed. H. Bundgaard, Elsevier, 1985. Prodrugs include, but are not limited to, esters, amides, sulfonates, and phosphonate esters.

The present invention also relates to pharmaceutically active metabolites of compounds of Formula I or II, and uses of such metabolites in the methods of the invention. A "pharmaceutically active metabolite" means a pharmacologically active product of metabolism in the body of a compound of Formula I or II, or salts thereof. Prodrugs and active metabolites of a compound may be determined using routine techniques known or available in the art. See, e.g., Bertolini et al., *J. Med. Chem.* 1997, 40, 2011-2016; Shan et al., *J. Pharm. Sci.* 1997, 86 (7), 765-767; Bagshawe, *Drug*

Dev. Res. 1995, 34, 220-230; Bodor, Adv. Drug Res. 1984, 13, 255-331; Bundgaard, Design of Prodrugs (Elsevier Press, 1985); and Larsen, Design and Application of Prodrugs, Drug Design and Development (Krogsgaard-Larsen et al., eds., Harwood Academic Publishers, 1991).

Any formula given herein is also intended to represent unlabeled forms as well as isotopically labeled forms of the compounds. Isotopically labeled compounds have structures depicted by the formulas given herein except that one or more atoms are replaced by an atom having a selected atomic mass or mass number. Examples of isotopes that can be incorporated into compounds of the invention include isotopes of hydrogen, carbon, nitrogen, oxygen, phosphorous, fluorine, chlorine, and iodine, such as $^{2}$H, $^{3}$H, $^{11}$C, $^{13}$C, $^{14}$C, $^{15}$N, $^{18}$O, $^{17}$O, $^{31}$P, $^{32}$P, $^{35}$S, $^{18}$F, $^{36}$Cl, and $^{125}$I, respectively. Such isotopically labelled compounds are useful in metabolic studies (for example with $^{14}$C), reaction kinetic studies (with, for example $^{2}$H or $^{3}$H), detection or imaging techniques [such as positron emission tomography (PET) or single-photon emission computed tomography (SPECT)] including drug or substrate tissue distribution assays, or in radioactive treatment of patients. In particular, an $^{18}$F or $^{11}$C labeled compound may be particularly suitable for PET or SPECT studies. Further, substitution with heavier isotopes such as deuterium (i.e., $^{2}$H) may afford certain therapeutic advantages resulting from greater metabolic stability, for example increased in vivo half-life or reduced dosage requirements. Isotopically labeled compounds of this invention and prodrugs thereof can generally be prepared by carrying out the procedures disclosed in the schemes or in the examples and preparations described below by substituting a readily available isotopically labeled reagent for a non-isotopically labeled reagent. Further, substitution with heavier isotopes such as deuterium (i.e., $^{2}$H) may afford certain therapeutic advantages resulting from greater metabolic stability, for example increased in vivo half-life or reduced dosage requirements. Isotopically labeled compounds of this invention and prodrugs thereof can generally be prepared by carrying out the procedures disclosed in the schemes or in the examples and preparations described below by substituting a readily available isotopically labeled reagent for a non-isotopically labeled reagent.

The use of the terms "salt," "solvate," "polymorph," "prodrug," and the like, with respect to the compounds described herein is intended to apply equally to the salt, solvate, polymorph, and prodrug forms of enantiomers, stereoisomers, rotamers, tautomers, atropisomers, and racemates of the inventive compounds.

Also contemplated herein are methods of synthesizing compounds of Formula I or II.

Compounds of the Invention

The invention provides compounds of formula I

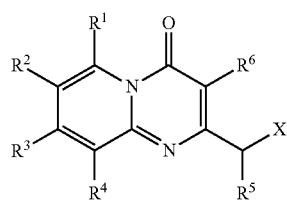

I or pharmaceutically acceptable salts thereof, wherein:
X is:
 —O—Ar;
 —NR$^a$—Ar; or
 —Ar;
R$^1$ is:
 hydrogen;
 C$_{1-6}$alkyl;
 halo;
 C$_{1-6}$alkoxy;
 cyano;
 heteroaryl selected from furanyl, thienyl, pyrrolyl, pyrazolyl, imidazolyl, pyridinyl and pyrimidinyl, each of which may be unsubstituted or substituted once or twice with R$^b$;
 —C(O)—NHR$^c$;
 —C(O)—R$^c$; or
 cyclopropyl which may be unsubstituted or substituted once or twice with R$^d$;
R$^2$ is:
 hydrogen;
 C$_{1-6}$alkyl;
 C$_{1-6}$alkoxy;
 halo; or
 halo-C$_{1-6}$alkyl;
R$^3$ is:
 hydrogen;
 C$_{1-6}$alkyl;
 C$_{1-6}$alkoxy;
 halo; or
 halo-C$_{1-6}$alkyl;
R$^4$ is:
 hydrogen; or
 C$_{1-6}$alkyl;
R$^5$ is:
 hydrogen; or
 C$_{1-6}$alkyl; and
R$^6$ is:
 hydrogen;
 C$_{1-6}$alkyl;
Ar is: phenyl; or heteroaryl selected from furanyl, thienyl, pyrrolyl, pyrazolyl, imidazolyl, benzimidazolyl, pyridinyl and pyrimidinyl, wherein the phenyl or heteroaryl may be unsubstituted or substituted one, two or three times with R$^e$;
R$^a$ is:
 hydrogen; or
 C$_{1-6}$alkyl;
each R$^b$ is independently:
 C$_{1-6}$alkyl;
 halo;
 halo-C$_{1-6}$alkyl; or
 cyclopropyl;
R$^c$ is:
 C$_{1-6}$alkyl; or
 halo-C$_{1-6}$alkyl;
R$^d$ is:
 C$_{1-6}$alkyl;
 halo;
 halo-C$_{1-6}$alkyl;
 hydroxy-C$_{1-6}$alkyl;
 C$_{1-6}$alkoxy-C$_{1-6}$alkyl; or
 cyano;
each R$^e$ is independently:
 C$_{1-6}$alkyl;
 halo;
 halo-C$_{1-6}$alkyl;
 —NH—C(O)—R$^f$;
 cyano; or
 cyclopropyl; and
R$^f$ is furanyl, thienyl, pyrrolyl, pyrazolyl or imidazolyl.

In certain embodiments, X is —O—Ar.
In certain embodiments, X is —NR$^a$—Ar.
In certain embodiments, X is Ar.
In certain embodiments, R$^1$ is: C$_{1-6}$alkyl; halo; C$_{1-6}$alkoxy; cyano; heteroaryl selected from furanyl, thienyl, pyrrolyl, pyrazolyl, imidazolyl, pyridinyl and pyrimidinyl, each of which may be unsubstituted or substituted once or twice with R$^b$; —C(O)—NHR$^c$; —C(O)—R$^c$; or cyclopropyl which may be unsubstituted or substituted once or twice with R$^d$.

In certain embodiments, R$^1$ is: C$_{1-6}$alkyl; halo; C$_{1-6}$alkoxy; cyano; or cyclopropyl which may be unsubstituted or substituted once or twice with R$^d$.

In certain embodiments, R$^1$ is: halo; C$_{1-6}$alkoxy; cyano; heteroaryl selected from furanyl, thienyl, pyrrolyl, pyrazolyl, imidazolyl, pyridinyl and pyrimidinyl, each of which may be unsubstituted or substituted once or twice with R$^b$; —C(O)—NHR$^c$; —C(O)—R$^c$; or cyclopropyl which may be unsubstituted or substituted once or twice with R$^d$.

In certain embodiments, R$^1$ is: C$_{1-6}$alkoxy; cyano; heteroaryl selected from furanyl, thienyl, pyrrolyl, pyrazolyl, imidazolyl, pyridinyl and pyrimidinyl, each of which may be unsubstituted or substituted once or twice with R$^b$; —C(O)—NHR$^c$; —C(O)—R$^c$; or cyclopropyl which may be unsubstituted or substituted once or twice with R$^d$.

In certain embodiments, R$^1$ is: halo; C$_{1-6}$alkoxy; cyano; or cyclopropyl which may be unsubstituted or substituted once or twice with R$^d$.

In certain embodiments, R$^1$ is: C$_{1-6}$alkoxy; cyano; or cyclopropyl which may be unsubstituted or substituted once or twice with R$^d$.

In certain embodiments, R$^1$ is hydrogen.
In certain embodiments, R$^1$ is C$_{1-6}$alkyl.
In certain embodiments, R$^1$ is halo.
In certain embodiments, R$^1$ is C$_{1-6}$alkoxy.
In certain embodiments, R$^1$ is cyano.
In certain embodiments, R$^1$ is heteroaryl selected from furanyl, thienyl, pyrrolyl, pyrazolyl, imidazolyl, pyridinyl and pyrimidinyl, each of which may be unsubstituted or substituted once or twice with R$^b$.
In certain embodiments, R$^1$ is furanyl, pyrazolyl, or pyrimidinyl, each of which may be unsubstituted or substituted once or twice with R$^b$.
In certain embodiments, R$^1$ is furanyl which may be unsubstituted or substituted once or twice with R$^b$.
In certain embodiments, R$^1$ is thienyl which may be unsubstituted or substituted once or twice with R$^b$.
In certain embodiments, R$^1$ is pyrrolyl which may be unsubstituted or substituted once or twice with R$^b$.
In certain embodiments, R$^1$ is pyrazolyl which may be unsubstituted or substituted once or twice with R$^b$.
In certain embodiments, R$^1$ is imidazolyl which may be unsubstituted or substituted once or twice with R$^b$.
In certain embodiments, R$^1$ is pyridinyl which may be unsubstituted or substituted once or twice with R$^b$.
In certain embodiments, R$^1$ is pyrimidinyl which may be unsubstituted or substituted once or twice with R$^b$.
In certain embodiments, R$^1$ is —C(O)—NHR$^c$.
In certain embodiments, R$^1$ is —C(O)—R$^c$.
In certain embodiments, R$^1$ is cyclopropyl which may be unsubstituted or substituted once or twice with R$^d$.
In certain embodiments, R$^1$ is cyclopropyl substituted once with cyano.
In certain embodiments, R$^1$ is cyclopropanecarbonitrile.
In certain embodiments, R$^2$ is hydrogen, halo or C$_{1-6}$alkyl.
In certain embodiments, R$^2$ is hydrogen.
In certain embodiments, R$^2$ is hydrogen or C$_{1-6}$alkyl.
In certain embodiments, R$^2$ is hydrogen or C$_{1-6}$alkoxy.
In certain embodiments, R$^2$ is hydrogen or halo.
In certain embodiments, R$^2$ is hydrogen or halo-C$_{1-6}$alkyl.
In certain embodiments, R$^2$ is C$_{1-6}$alkyl.
In certain embodiments, R$^2$ is C$_{1-6}$alkoxy.
In certain embodiments, R$^2$ is halo.
In certain embodiments, R$^2$ is halo-C$_{1-6}$alkyl.
In certain embodiments, R$^3$ is hydrogen, C$_{1-6}$alkyl or halo-C$_{1-6}$alkyl.
In certain embodiments, R$^3$ is hydrogen.
In certain embodiments, R$^3$ is hydrogen or C$_{1-6}$alkyl.
In certain embodiments, R$^3$ is hydrogen or C$_{1-6}$alkoxy.
In certain embodiments, R$^3$ is hydrogen or halo.
In certain embodiments, R$^3$ is hydrogen or halo-C$_{1-6}$alkyl.
In certain embodiments, R$^3$ is C$_{1-6}$alkyl.
In certain embodiments, R$^3$ is C$_{1-6}$alkoxy.
In certain embodiments, R$^3$ is halo.
In certain embodiments, R$^3$ is halo-C$_{1-6}$alkyl.
In certain embodiments, R$^4$ is hydrogen.
In certain embodiments, R$^4$ is C$_{1-6}$alkyl.
In certain embodiments, R$^5$ is hydrogen.
In certain embodiments, R$^5$ is C$_{1-6}$alkyl.
In certain embodiments, R$^6$ is hydrogen.
In certain embodiments, R$^6$ is C$_{1-6}$alkyl.
In certain embodiments, Ar is phenyl or pyrazolyl, each of which may be unsubstituted or substituted one or two times with R$^e$;
In certain embodiments, Ar is phenyl which may be unsubstituted or substituted one or two times with R$^e$.
In certain embodiments, Ar is furanyl which may be unsubstituted or substituted one or two times with R$^e$.
In certain embodiments, Ar is thienyl which may be unsubstituted or substituted one or two times with R$^e$.
In certain embodiments, Ar is pyrrolyl which may be unsubstituted or substituted one or two times with R$^e$.
In certain embodiments, Ar is pyrazolyl which may be unsubstituted or substituted one or two times with R$^e$.
In certain embodiments, Ar is imidazolyl which may be unsubstituted or substituted one or two times with R$^e$.
In certain embodiments, Ar is benzimidazolyl which may be unsubstituted or substituted one or two times with R$^e$.
In certain embodiments, Ar is pyridinyl which may be unsubstituted or substituted one or two times with R$^e$.
In certain embodiments, Ar is pyrimidinyl which may be unsubstituted or substituted one or two times with R$^e$.
In certain embodiments, Ar is pyrazolyl substituted one or two times with R$^e$.
In certain embodiments, Ar is 3-chloro-5-(trifluoromethyl)pyrazol-1-yl.
In certain embodiments, R$^a$ is hydrogen.
In certain embodiments, R$^a$ is C$_{1-6}$alkyl.
In certain embodiments, R$^b$ is C$_{1-6}$alkyl.
In certain embodiments, R$^b$ is halo.
In certain embodiments, R$^b$ is halo-C$_{1-6}$alkyl.
In certain embodiments, R$^b$ is cyclopropyl.
In certain embodiments, R$^c$ is hydrogen.
In certain embodiments, R$^c$ is C$_{1-6}$alkyl.
In certain embodiments, each R$^d$ is independently cyano, C$_{1-6}$alkyl or hydroxy-C$_{1-6}$alkyl.
In certain embodiments, each R$^d$ is independently cyano or hydroxy-C$_{1-6}$alkyl
In certain embodiments, R$^d$ is C$_{1-6}$alkyl.
In certain embodiments, R$^d$ is halo.
In certain embodiments, R$^d$ is halo-C$_{1-6}$alkyl.
In certain embodiments, R$^d$ is hydroxy-C$_{1-6}$alkyl.

In certain embodiments, $R^d$ is $C_{1-6}$alkoxy-$C_{1-6}$alkyl.

In certain embodiments, $R^d$ is cyano.

In certain embodiments, each $R^e$ is independently halo or halo-$C_{1-6}$alkyl.

In certain embodiments, $R^e$ is $C_{1-6}$alkyl.

In certain embodiments, $R^e$ is halo.

In certain embodiments, $R^e$ is halo-$C_{1-6}$alkyl.

In certain embodiments, $R^e$ is —NH—C(O)—$R^f$.

In certain embodiments, $R^e$ is cyano.

In certain embodiments, $R^e$ is cyclopropyl.

In certain embodiments, $R^f$ is furanyl.

In certain embodiments, $R^f$ is thienyl.

In certain embodiments, $R^f$ is pyrrolyl.

In certain embodiments, $R^f$ is pyrazolyl.

In certain embodiments, $R^f$ is imidazolyl.

In certain embodiments, the compound of formula I may be a compound of formula II

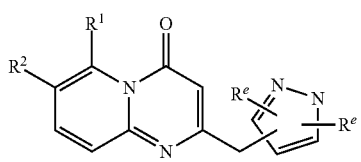

II wherein $R^1$, $R^2$, $R^b$ and $R^e$ are as defined herein.

In certain embodiments, the compound of formula I may be a compound of formula III

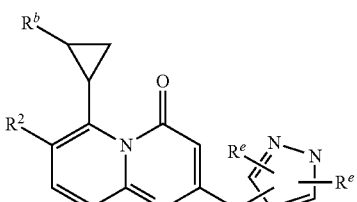

III wherein $R^2$, $R^b$ and $R^e$ are as defined herein.

In certain embodiments, the compound of formula I may be a compound of formula IV

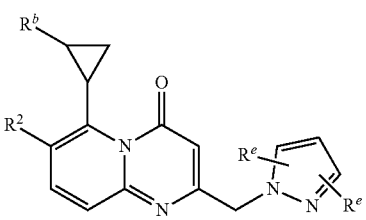

IV wherein $R^2$, $R^b$ and $R^e$ are as defined herein.

In certain embodiments, the compound of formula I may be a compound of formula V

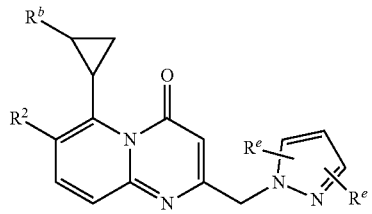

V wherein $R^2$, $R^b$ and $R^e$ are as defined herein.

In certain embodiments, the compound of formula I may be a compound of formula VI

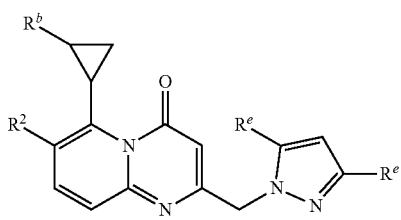

VI wherein $R^2$, $R^b$ and $R^e$ are as defined herein.

In certain embodiments, the compound of formula I may be a compound of formula VIa, VIb, VIc, or VId.

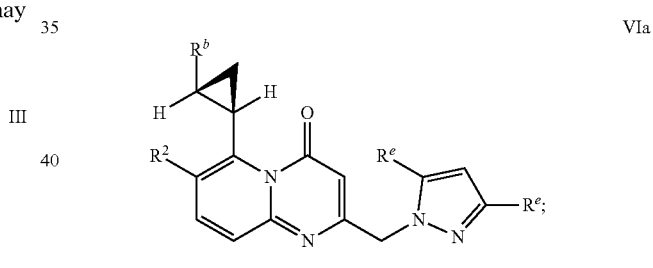

VIa

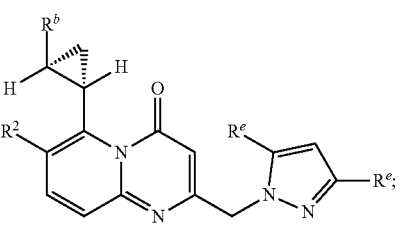

VIb

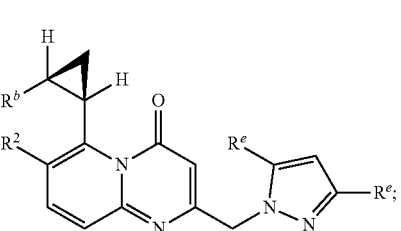

VIc

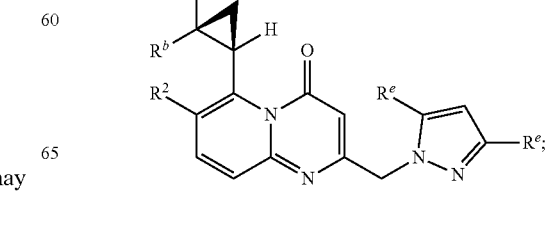

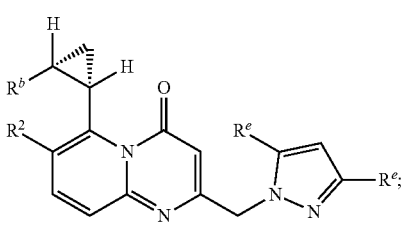

VId wherein $R^2$, $R^b$ and $R^e$ are as defined herein.

In certain embodiments, the compound is of formula VIa.
In certain embodiments, the compound is of formula VIb.
In certain embodiments, the compound is of formula VIc.
In certain embodiments, the compound is of formula VId.

Methods

The invention also provides a method for treating a disease or condition mediated by or otherwise associated with an NR2A positive allosteric modulator, the method comprising administering to a subject in need thereof an effective amount of a compound of the invention.

The disease may be schizophrenia, Alzheimer's disease, Parkinson's disease, anxiety, depression, cognitive disorder, memory disorder, memory loss, eating disorders, attention deficit disorders, and akisthesia.

The compounds of the invention may also be used to improve cognitive function and cognitive memory.

Representative compounds in accordance with the methods of the invention are shown in the experimental examples below.

Synthesis

Compounds of the present invention can be made by a variety of methods depicted in the illustrative synthetic reaction schemes shown and described below.

The starting materials and reagents used in preparing these compounds generally are either available from commercial suppliers, such as Aldrich Chemical Co., or are prepared by methods known to those skilled in the art following procedures set forth in references such as *Fieser and Fieser's Reagents for Organic Synthesis*; Wiley & Sons: New York, 1991, Volumes 1-15; *Rodd's Chemistry of Carbon Compounds*, Elsevier Science Publishers, 1989, Volumes 1-5 and Supplementals; and *Organic Reactions*, Wiley & Sons: New York, 1991, Volumes 1-40. The following synthetic reaction schemes are merely illustrative of some methods by which the compounds of the present invention can be synthesized, and various modifications to these synthetic reaction schemes can be made and will be suggested to one skilled in the art having referred to the disclosure contained in this Application.

The starting materials and the intermediates of the synthetic reaction schemes can be isolated and purified if desired using conventional techniques, including but not limited to, filtration, distillation, crystallization, chromatography, and the like. Such materials can be characterized using conventional means, including physical constants and spectral data.

Unless specified to the contrary, the reactions described herein may be conducted under an inert atmosphere at atmospheric pressure at a reaction temperature range of from about −78° C. to about 150° C., for example, from about 0° C. to about 125° C., or conveniently at about room (or ambient) temperature, e.g., about 20° C.

Scheme A below illustrates one synthetic procedure usable to prepare specific compounds of formula I, wherein R is lower alkyl, X is halo and may be the same or different upon each occurrence, and $R^1$, $R^2$, $R^3$, $R^4$, $R^5$, $R^6$, $R^d$ and $R^e$ are as defined herein.

SCHEME A

In step 1 of Scheme A, aminopyridine compound a is treated with oxobutanoate b in the presence of polyphosphoric acid to effect a ring forming reaction and provide pyridopyrimidone intermediate compound c.

Pyrido-pyrimidone intermediate c is then reacted with pyrazole compound d in step 2 under polar aprotic solvent conditions to afford pyrazolo-pyridopyrimidone intermediate compound e.

In step 3, compound e is reacted with trifluoroborate reagent in the presence of a suitable palladium catalyst, under polar protic solvent conditions, to afford pyrazolo-pyridopyrimidone compound g, which is a compound of formula I in accordance with the invention.

Many variations on the procedure of Scheme A are possible and will suggest themselves to those skilled in the art. For example, compound a could be treated with trifluoroborate reagent f prior to step 1. Trifluoroborate reagent f could be replaced by a corresponding boronate ester reagent (not shown). Additional details usable in Scheme A are provided in the Experimental section below.

Pharmaceutical Compositions

Additional embodiments include pharmaceutical compositions comprising at least one compound of Formula III, or a pharmaceutically acceptable salt thereof, and a pharmaceutically acceptable excipient, and a method of treating a subject suffering from a disease or medical condition mediated by NMDA receptor activity, comprising administering to the subject in need of such treatment an effective amount of at least one compound of Formula III, or a pharmaceutically acceptable salt thereof.

Embodiments of the invention also include compounds in which each variable is defined independently as described above.

In certain embodiments, the compound of Formula I is a compound selected from the group consisting of the compounds in Table 1, and pharmaceutically acceptable salts thereof:

Pharmaceutical Description

As used herein, the term "subject" encompasses mammals and non-mammals. Examples of mammals include, but are not limited to, any member of the Mammalian class: humans; non-human primates such as chimpanzees, and other apes and monkey species; farm animals such as cattle, horses, sheep, goats, swine; domestic animals such as rabbits, dogs, and cats; and laboratory animals including rodents, such as rats, mice and guinea pigs, and the like. Examples of non-mammals include, but are not limited to, birds, fish and the like. In one embodiment of the present invention, the mammal is a human.

"Patient" encompasses a human or animal subject.

The term "inhibitor" refers to a molecule such as a compound, a drug, an enzyme activator, or a hormone that blocks or otherwise interferes with a particular biologic activity.

The term "modulator" refers to a molecule, such as a compound of the present invention, that increases or decreases, or otherwise affects the activity of a given enzyme or protein.

As used herein, the terms "treat" or "treatment" encompass both "preventative" and "curative" treatment. "Preventative" treatment is meant to indicate a postponement of development of a disease, a symptom of a disease, or medical condition, suppressing symptoms that may appear, or reducing the risk of developing or recurrence of a disease or symptom. "Curative" treatment includes reducing the severity of or suppressing the worsening of an existing disease, symptom, or condition. Thus, treatment includes ameliorating or preventing the worsening of existing disease symptoms, preventing additional symptoms from occurring, ameliorating or preventing the underlying metabolic causes of symptoms, inhibiting the disorder or disease, e.g., arresting the development of the disorder or disease, relieving the disorder or disease, causing regression of the disorder or disease, relieving a condition caused by the disease or disorder, or stopping the symptoms of the disease or disorder.

The terms "effective amount" or "therapeutically effective amount" refer to a sufficient amount of the agent to provide the desired biological result. That result can be reduction and/or alleviation of the signs, symptoms, or causes of a disease or medical condition, or any other desired alteration of a biological system. For example, an "effective amount" for therapeutic use is the amount of a compound, or of a composition comprising the compound, that is required to provide a clinically relevant change in a disease state, symptom, or medical condition. An appropriate "effective" amount in any individual case may be determined by one of ordinary skill in the art using routine experimentation. Thus, the expression "effective amount" generally refers to the quantity for which the active substance has a therapeutically desired effect. Effective amounts or doses of the compounds of the embodiments may be ascertained by routine methods, such as modeling, dose escalation, or clinical trials, taking into account routine factors, e.g., the mode or route of administration or drug delivery, the pharmacokinetics of the agent, the severity and course of the infection, the subject's health status, condition, and weight, and the judgment of the treating physician. An exemplary dose is in the range of about 1 µg to 2 mg of active agent per kilogram of subject's body weight per day, preferably about 0.05 to 100 mg/kg/day, or about 1 to 35 mg/kg/day, or about 0.1 to 10 mg/kg/day. The total dosage may be given in single or divided dosage units (e.g., BID, TID, QID).

Once improvement of the patient's disease has occurred, the dose may be adjusted for preventative or maintenance treatment. For example, the dosage or the frequency of administration, or both, may be reduced as a function of the symptoms, to a level at which the desired therapeutic or prophylactic effect is maintained. Of course, if symptoms have been alleviated to an appropriate level, treatment may cease. Patients may, however, require intermittent treatment on a long-term basis upon any recurrence of symptoms. Patients may also require chronic treatment on a long-term basis.

A pharmaceutical composition according to the invention comprises at least one compound of Formula (I), or a pharmaceutically acceptable salt thereof. The pharmaceutical compositions may further comprise one or more pharmaceutically-acceptable excipients. A pharmaceutically-acceptable excipient is a substance that is non-toxic and otherwise biologically suitable for administration to a subject. Such excipients facilitate administration of the compounds described herein and are compatible with the active ingredient. Examples of pharmaceutically-acceptable excipients include stabilizers, lubricants, anti-caking agents, glidants, surfactants, diluents, anti-oxidants, binders, chelating agents, coating agents, coloring agents, bulking agents, emulsifiers, buffers, pH modifiers, or taste-modifying agents. In preferred embodiments, pharmaceutical compositions according to the embodiments are sterile compositions. Sterile compositions include compositions that are in accord with national and local regulations governing such compositions. Pharmaceutical compositions may be prepared using compounding techniques known or that become available to those skilled in the art.

The pharmaceutical compositions and compounds described herein may be formulated as solutions, emulsions, suspensions, dispersions, or inclusion complexes such as cyclodextrins in suitable pharmaceutical solvents or carriers, or as pills, tablets, lozenges, suppositories, sachets, dragees, granules, powders, powders for reconstitution, or capsules along with solid carriers according to conventional methods known in the art for preparation of various dosage forms. Pharmaceutical compositions of the embodiments may be administered by a suitable route of delivery, such as oral, parenteral, rectal, nasal, topical, or ocular routes, or by inhalation. Preferably, the compositions are formulated for intravenous or oral administration.

A further embodiment of the invention is a method of preparing a pharmaceutical formulation comprising mixing at least one compound of the present invention, and, optionally, one or more pharmaceutically acceptable excipients.

In certain aspects, the invention relates to methods of treating diseases or conditions mediated by activation or deactivation of NMDA receptors, or which are generally mediated by NMDA receptor activity. Such disease or condition is one or more selected from the group consisting of pain, neuropathic pain, inflammatory pain, peripheral neuropathy, stroke, epilepsy, neurodegeneration, schizophrenia, drug addiction, mood disorders, post-traumatic stress disorder, seizures, convulsions, age-associated memory impairment, depression, stroke, traumatic brain injury, ischemia, Alzheimer's disease, Parkinson's disease, Huntington's disease, amyotrophic lateral sclerosis, or Creutzfeldt-Jakob disease. In particular, the disease or condition is schizophrenia.

Still another aspect of this invention is to provide a method for treating, preventing, inhibiting or eliminating a disease or condition in a patient by modulating, activating, or inhibiting NMDA receptor activity in said patient by administering a therapeutically effective amount of at least one compound of this disclosure, wherein said disease or condition is selected from the group consisting of pain, neuropathic pain, inflammatory pain, peripheral neuropathy, stroke, epilepsy, neurodegeneration, schizophrenia, drug addiction, mood disorders, post-traumatic stress disorder, seizures, convulsions, age-associated memory impairment, depression, stroke, traumatic brain injury, ischemia, Alzheimer's disease, Parkinson's disease, Huntington's disease, amyotrophic lateral sclerosis, or Creutzfeldt-Jakob disease.

Still another aspect of this invention is the use of a compound as described herein as a positive allosteric modulator (PAM) of an NMDA receptor. The invention includes a method of modulating and/or amplifying the activity an NMDA receptor by contacting the receptor at an allosteric binding site with at least one compound as described herein or a pharmaceutical composition comprising such a compound. Further, compounds of the invention are useful as subtype selective for NR2A-containing NMDA receptors. The invention is also directed toward a method of modulating an NR2A-containing NMDA receptor by contacting the receptor with at least one compound of the invention or a pharmaceutical composition comprising such a compound.

The pharmaceutical compositions and compounds described herein may be formulated as solutions, emulsions, suspensions, dispersions, or inclusion complexes such as cyclodextrins in suitable pharmaceutical solvents or carriers, or as pills, tablets, lozenges, suppositories, sachets, dragees, granules, powders, powders for reconstitution, or capsules along with solid carriers according to conventional methods known in the art for preparation of various dosage forms. Pharmaceutical compositions of the embodiments may be administered by a suitable route of delivery, such as oral, parenteral, rectal, nasal, topical, or ocular routes, or by inhalation. Preferably, the compositions are formulated for intravenous or oral administration.

For oral administration, the compounds the embodiments may be provided in a solid form, such as a tablet or capsule, or as a solution, emulsion, or suspension. To prepare the oral compositions, the compounds of the embodiments may be formulated to yield a dosage of, e.g., from about 0.01 to about 50 mg/kg daily, or from about 0.05 to about 20 mg/kg daily, or from about 0.1 to about 10 mg/kg daily. Oral tablets may include the active ingredient(s) mixed with compatible pharmaceutically acceptable excipients such as diluents, disintegrating agents, binding agents, lubricating agents, sweetening agents, flavoring agents, coloring agents and preservative agents. Suitable inert fillers include sodium and calcium carbonate, sodium and calcium phosphate, lactose, starch, sugar, glucose, methyl cellulose, magnesium stearate, mannitol, sorbitol, and the like. Exemplary liquid oral excipients include ethanol, glycerol, water, and the like. Starch, polyvinyl-pyrrolidone (PVP), sodium starch glycolate, microcrystalline cellulose, and alginic acid are exemplary disintegrating agents. Binding agents may include starch and gelatin. The lubricating agent, if present, may be magnesium stearate, stearic acid, or talc. If desired, the tablets may be coated with a material such as glyceryl monostearate or glyceryl distearate to delay absorption in the gastrointestinal tract, or may be coated with an enteric coating.

Capsules for oral administration include hard and soft gelatin capsules. To prepare hard gelatin capsules, active ingredient(s) may be mixed with a solid, semi-solid, or liquid diluent. Soft gelatin capsules may be prepared by mixing the active ingredient with water, an oil such as peanut oil or olive oil, liquid paraffin, a mixture of mono and di-glycerides of short chain fatty acids, polyethylene glycol 400, or propylene glycol.

Liquids for oral administration may be in the form of suspensions, solutions, emulsions, or syrups, or may be lyophilized or presented as a dry product for reconstitution with water or other suitable vehicle before use. Such liquid compositions may optionally contain: pharmaceutically-acceptable excipients such as suspending agents (for example, sorbitol, methyl cellulose, sodium alginate, gelatin, hydroxyethylcellulose, carboxymethylcellulose, aluminum stearate gel and the like); non-aqueous vehicles, e.g., oil (for example, almond oil or fractionated coconut oil), propylene glycol, ethyl alcohol, or water; preservatives (for example, methyl or propyl p-hydroxybenzoate or sorbic acid); wetting agents such as lecithin; and, if desired, flavoring or coloring agents.

The inventive compositions may be formulated for rectal administration as a suppository. For parenteral use, including intravenous, intramuscular, intraperitoneal, intranasal, or subcutaneous routes, the agents of the embodiments may be provided in sterile aqueous solutions or suspensions, buffered to an appropriate pH and isotonicity or in parenterally acceptable oil. Suitable aqueous vehicles include Ringer's solution and isotonic sodium chloride. Such forms may be presented in unit-dose form such as ampoules or disposable injection devices, in multi-dose forms such as vials from which the appropriate dose may be withdrawn, or in a solid form or pre-concentrate that can be used to prepare an injectable formulation. Illustrative infusion doses range from about 1 to 1000 μg/kg/minute of agent admixed with a pharmaceutical carrier over a period ranging from several minutes to several days.

For nasal, inhaled, or oral administration, the inventive pharmaceutical compositions may be administered using, for example, a spray formulation also containing a suitable carrier.

For topical applications, the compounds of the present embodiments are preferably formulated as creams or ointments or a similar vehicle suitable for topical administration. For topical administration, the inventive compounds may be mixed with a pharmaceutical carrier at a concentration of about 0.1% to about 10% of drug to vehicle. Another mode of administering the agents of the embodiments may utilize a patch formulation to effect transdermal delivery.

The actual dosage employed may be varied depending upon the requirements of the patient and the severity of the condition being treated. Determination of the proper dosage regimen for a particular situation is within the skill of the art.

For convenience, the total daily dosage may be divided and administered in portions during the day as required.

The amount and frequency of administration of the compounds of the invention and/or the pharmaceutically acceptable salts thereof will be regulated according to the judgment of the attending clinician considering such factors as age, condition and size of the patient as well as severity of the symptoms being treated. A typical recommended daily dosage regimen for oral administration can range from about 1 mg/day to about 500 mg/day, preferably 1 mg/day to 200 mg/day, in two to four divided doses.

Still another embodiment of the invention is a pharmaceutical formulation comprising at least one compound of Formula I or II, or a pharmaceutically acceptable salt thereof, and a pharmaceutically acceptable excipient, and further comprising one or more adjunctive active agent. Methods of treatment as described herein include regimes in which the compound of the invention and at least one adjunctive active agent are administered simultaneously or sequentially.

The expression "adjunctive active agent" generally refers to agents which targets the same or a different disease, symptom, or medical condition as the primary therapeutic agent. Adjunctive active agents may treat, alleviate, relieve, or ameliorate side effects caused by administration of the primary therapeutic agents.

Examples

Exemplary, non-limiting, chemical entities and methods useful in preparing compounds of the invention will now be described by reference to the specific examples that follow. Those skilled in the art will appreciate that other synthetic routes may be used to synthesize the compounds according to the invention. Although specific starting materials and reagents are depicted and discussed herein, other starting materials and reagents can be easily substituted to provide a variety of derivatives and/or reaction conditions. In addition, many of the exemplary compounds prepared by the described methods can be further modified in light of this disclosure using conventional chemistry well known to those skilled in the art.

Artisans will recognize that, to obtain the various compounds herein, starting materials may be suitably selected so that the ultimately desired substituents will be carried through the reaction scheme with or without protection as appropriate to yield the desired product. Alternatively, it may be necessary or desirable to employ, in the place of the ultimately desired substituent, a suitable group that may be carried through the reaction scheme and replaced as appropriate with the desired substituent. Each of the reactions depicted in the reaction schemes is preferably run at a temperature from about 0° C. to the reflux temperature of the solvent used.

In the methods of preparing compounds according to the invention, it may be advantageous to separate reaction products from one another and/or from starting materials. The desired products of each step or series of steps may be separated and/or purified to the desired degree of homogeneity by the techniques common in the art. Typically such separations involve multiphase extraction, crystallization from a solvent or solvent mixture, distillation, sublimation, or chromatography. Chromatography can involve any number of methods including, for example: reverse-phase and normal phase; size exclusion; ion exchange; high, medium and low pressure liquid chromatography methods and apparatus; small scale analytical; simulated moving bed (SMB) and preparative thin or thick layer chromatography, as well as techniques of small scale thin layer and flash chromatography.

Diastereomeric mixtures may be separated into their individual diastereomers on the basis of their physical chemical differences by methods well known to those skilled in the art, such as, for example, by chromatography and/or fractional crystallization. Enantiomers may be separated by converting the enantiomeric mixture into a diastereomeric mixture by reaction with an appropriate optically active compound (e.g., chiral auxiliary such as a chiral alcohol or Mosher's acid chloride, or formation of a mixture of diastereomeric salts, for example, with tartaric acid or a chiral amine), separating the diastereomers by, for example, fractional crystallization or chromatography, and converting (e.g., hydrolyzing or de-salting) the individual diastereomers to the corresponding pure enantiomers. Enantiomers may also be separated by use of chiral HPLC column or prepared directly by chiral synthesis. The chiral centers of compounds of the present invention may be designated as "R" or "S" as defined by the IUPAC 1974 Recommendations. Enriched or purified enantiomers can be distinguished by methods used to distinguish other chiral molecules with asymmetric carbon atoms, such as optical rotation and circular dichroism.

General Experimental Conditions

Unless otherwise indicated, $^1$H NMR spectra were recorded at ambient temperature using a Varian Unity Inova (400 MHz) spectrometer with a triple resonance 5 mm probe. Chemical shifts are expressed in ppm relative to tetramethylsilane. The following abbreviations have been used: br=broad signal, s=singlet, d=doublet, dd=double doublet, t=triplet, q=quartet, m=multiplet.

Microwave experiments were carried out using a CEM Discover, Smith Synthesiser or a Biotage Initiator 60™, which uses a single-mode resonator and dynamic field tuning, both of which give reproducibility and control. Temperatures from 40-250° C. can be achieved and pressures of up to 30 bars can be reached.

High Pressure Liquid Chromatography—Mass Spectrometry (LCMS) experiments was used to detect associated mass ions. The spectrometers have an electrospray source operating in positive and negative ion mode. Additional detection was achieved using a Sedex 85 evaporative light scattering detector.

The following examples illustrate the preparation of representative compounds of the invention. Unless otherwise specified, all reagents and solvents were of standard commercial grade and were used without further purification. Those having skill in the art will recognize that the starting materials, reagents, and conditions described in the examples may be varied and additional steps employed to produce compounds encompassed by the present inventions.

Example 1 (1R,2R)-2-(7-chloro-2-[[5-chloro-3-(trifluoromethyl)-1H-pyrazol-1-yl]methyl]-4-oxo-4H-pyrido[1,2-a]pyrimidin-6-yl)cyclopropane-1-carbonitrile and (1S,2S)-2-(7-chloro-2-[[5-chloro-3-(trifluoromethyl)-1H-pyrazol-1-yl]methyl]-4-oxo-4H-pyrido[1,2-a]pyrimidin-6-yl)cyclopropane-1-carbonitrile

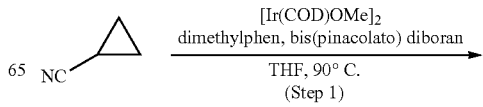

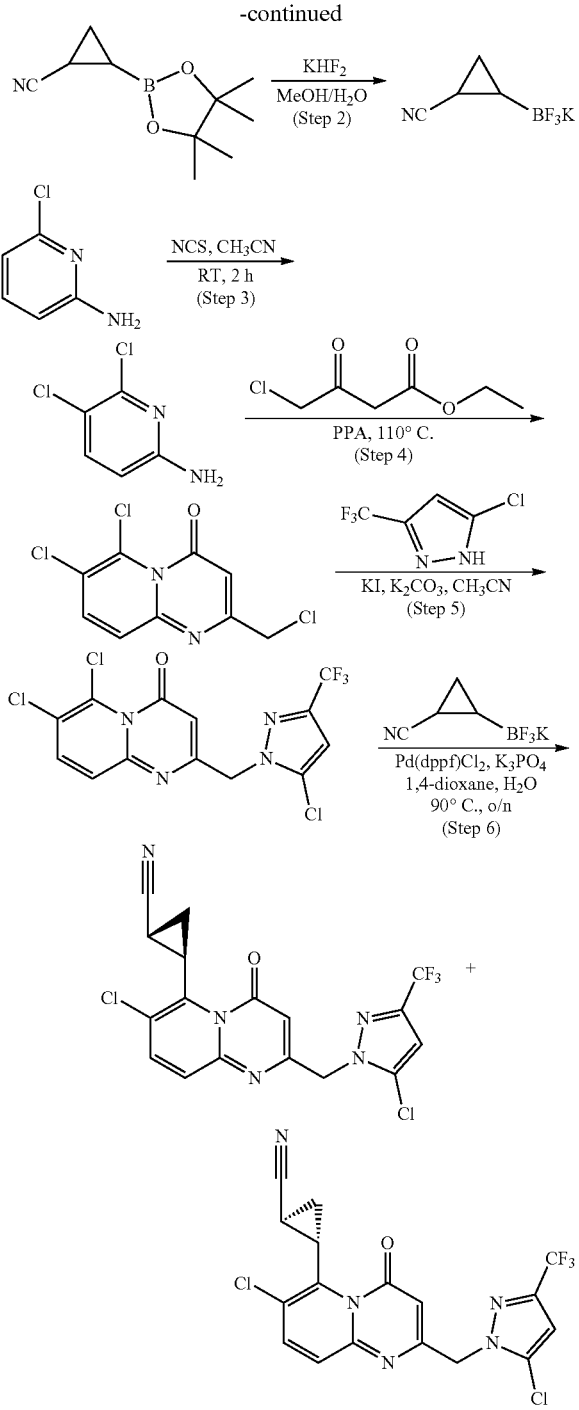

Step 1: 2-(tetramethyl-1,3,2-dioxaborolan-2-yl)cyclopropane-1-carbonitrile

Into a 30-mL sealed tube purged and maintained with an inert atmosphere of nitrogen a solution of cyclopropanecarbonitrile (1.0 g, 14.9 mmol) in tetrahydrofuran (12.2 mL) was added [Ir(COD)OMe]$_2$ (320 mg, 0.25 mmol), bis(pinacolato) diboron (1.59 g, 12.5 mmol) and dimethylphen (50.5 mg, 0.49 mmol). The reaction mixture was stirred at 90° C. for 18 h and concentrated in vacuo. The residue was purified by chromatography with ethyl acetate/petroleum ether (1:4) to afford 2-(tetramethyl-1,3,2-dioxaborolan-2-yl)cyclopropane-1-carbonitrile as a light yellow oil (1 g, crude). This reaction was repeated 180 times to provide 180 g of 2-(tetramethyl-1,3,2-dioxaborolan-2-yl)cyclopropane-1-carbonitrile as a light yellow oil.

Step 2: Potassium 2-(trifluoroborate)cyclopropanecarbonitrile

To a solution of 2-(tetramethyl-1,3,2-dioxaborolan-2-yl)cyclopropane-1-carbonitrile (180 g, crude) in methanol (4.5 L) was added difluorane potassium (9.98 g, 129 mmol) in H$_2$O (2 L). The resulting reaction mixture stirred at room temperature for 12 hours and concentrated in vacuo. The residue was washed with propan-2-one (6×1.5 L). The filtrate was concentrated in vacuo, dissolved with water (5 L), and washed with DCM (3×3 L) and EA (3×3 L). The water layer was freeze-dried to afford potassium 2-(trifluoroborate)cyclopropanecarbonitrile as a white solid (151.9 g, 33% in two steps). $^1$H-NMR (400 MHz, DMSO-d, ppm): δ 0.88-0.82 (m, 1H), 0.76-0.72 (m, 1H), 0.59-0.51 (m, 1H), 0.03-0.10 (m, 1H).

Step 3: 5,6-dichloropyridin-2-amine

To a solution of 6-chloropyridin-2-amine (5 g, 38.9 mmol) in acetonitrile (50 ml) was added N-chlorosuccinimide (5.25 g, 39.3 mmol). The reaction was stirred for 18 h at 80° C. and then concentrated in vacuo. The residue was purified by chromatography with ethyl acetate/petroleum ether (⅓) to afford 5,6-dichloropyridin-2-amine (4 g, 63%) as a white solid. LCMS (ESI): M+$^H$=163.0. $^1$HNMR (300 MHz, CDCl$_3$) δ 7.42 (d, J=4.0 Hz, 1H), 6.63 (d, J=4.0 Hz, 1H), 5.10 (brs, 2H).

Step 4: 6,7-Dichloro-2-(chloromethyl)-4H-pyrido[1,2-a]pyrimidin-4-one

A mixture of 5,6-dichloropyridin-2-amine (4 g, 24.5 mmol), ethyl 4-chloro-3-oxobutanoate (8.1 g, 49.2 mmol) and PPA (21 g, 182 mmol) was stirred for 1 h at 110° C. The reaction was poured into water (50 ml) and the pH value of the solution was adjusted to 7 with sodium hydroxide (1 mol/L). The resulting solution was extracted with dichloromethane (3×200 ml) and then concentrated in vacuo. The residue was purified by chromatography with ethyl acetate/petroleum ether (⅓) to afford 6,7-dichloro-2-(chloromethyl)-4H-pyrido[1,2-a]pyrimidin-4-one (2 g, 31%) as a brown solid. LCMS (ESI): M+$^H$=263.0. $^1$HNMR (300 MHz, CDCl$_3$) δ 7.58 (d, J=4.8 Hz, 1H), 7.37 (d, J=4.8 Hz, 1H), 6.57 (s, 1H), 4.45 (s, 2H).

Step 5: 6,7-Dichloro-2-[[5-chloro-3-(trifluoromethyl)-1H-pyrazol-1-yl]methyl]-4H-pyrido[1,2-a]pyrimidin-4-one To a solution of 6,7-dichloro-2-(chloromethyl)-4H-pyrido[1,2-a]pyrimidin-4-one (1 g, 3.80 mmol) in acetonitrile (50 mL) was added 5-chloro-3-(trifluoromethyl)-1H-pyrazole (519 mg, 3.04 mmol), potassium iodide (317 mg, 1.91 mmol) and potassium carbonate (1.05 g, 7.60 mmol). The reaction was stirred for 1 h at 80° C. Then the resulting mixture was concentrated in vacuo. The residue was purified by chromatography with ethyl acetate/petroleum ether (⅕) to afford 6,7-dichloro-2-[[5-chloro-3-(trifluoromethyl)-1H-pyrazol-1-yl]methyl]-4H-pyrido[1,2-a]pyrimidin-4-one (600 mg, 40%) as yellow oil. LCMS (ESI): M+H$^+$=397.1;

¹HNMR (300 MHz, CDCl₃) δ 7.60 (d, J=4.8 Hz, 1H), 7.34 (d, J=4.8 Hz, 1H), 6.60 (s, 1H), 5.85 (s, 1H), 5.31 (s, 2H).

(1R,2R)-2-(7-chloro-2-[[5-chloro-3-(trifluoromethyl)-1H-pyrazol-1-yl]methyl]-4-oxo-4H-pyrido[1,2-a]pyrimidin-6-yl)cyclopropane-1-carbonitrile and (1S,2R)-2-(7-chloro-2-[[5-chloro-3-(trifluoromethyl)-1H-pyrazol-1-yl]methyl]-4-oxo-4H-pyrido[1,2-a]pyrimidin-6-yl)cyclopropane-1-carbonitrile To a solution of 6,7-dichloro-2-[[5-chloro-3-(trifluoromethyl)-1H-pyrazol-1-yl]methyl]-4H-pyrido[1,2-a]pyrimidin-4-one (440 mg, 1.11 mmol) in 1,4-dioxane/H₂O (6 mL/0.6 mL) was added potassium 2-(trifluoroborate)cyclopropanecarbonitrile (577 mg, 3.34 mmol), 1,1'-Bis(diphenylphosphino)ferrocenepalladiumdichloride (250 mg, 0.342 mmol) and potassium phosphate (707 mg, 3.34 mmol). The resulting solution was stirred for 15 h at 90° C. and then concentrated in vacuo. The residue was purified with ethyl acetate/petroleum ether (⅛) to afford the racemic product (100 mg, 21%). Then this product was purified by Chiral-Prep-HPLC with the following conditions: Column, Chiralpak IC-3, 0.46*5 cm, 3 um; mobile phase, Hex and EtOH (hold 30.0% EtOH in 8 min); Detector, uv 254 nm to afford two isomers:

Enantiomer 1: (Retention time, 2.767 min)(1R,2R)-2-(7-chloro-2-[[5-chloro-3-(trifluoromethyl)-1H-pyrazol-1-yl]methyl]-4-oxo-4H-pyrido[1,2-a]pyrimidin-6-yl)cyclopropane-1-carbonitrile (42.3 mg, 9%) as a yellow solid. LCMS (ESI): M+H⁺=428.0; ¹HNMR (300 MHz, CDCl3) 7.52 (d, J=4.8 Hz, 1H), 7.37 (d, J=4.8 Hz, 1H), 6.64 (s, 1H), 5.86 (s, 1H), 5.34 (s, 2H), 3.32-3.24 (m, 1H), 1.88-1.77 (m, 1H), 1.57-1.50 (m, 1H), 1.28-1.22 (m, 1H).

Enantiomer 2: And (Retention time, 4.082 min) (1S,2S)-2-(7-chloro-2-[[5-chloro-3-(trifluoromethyl)-1H-pyrazol-1-yl]methyl]-4-oxo-4H-pyrido[1,2-a]pyrimidin-6-yl)cyclopropane-1-carbonitrile as a yellow solid (40.7 mg, 9%). LCMS (ESI): M+H⁺=428.0; ¹HNMR (300 MHz, CDCl₃) 7.54 (d, J=4.8 Hz, 1H), 7.41 (d, J=4.8 Hz, 1H), 6.64 (s, 1H), 5.85 (s, 1H), 5.35 (s, 2H), 3.32-3.25 (m, 1H), 1.89-1.82 (m, 1H), 1.57-1.51 (m, 1H), 1.27-1.20 (m, 1H).

Additional compounds made by the above procedure are shown in Table 1 below, together with EC₅₀ values and % from the assay below.

TABLE 1

| | Structure | Name | EC50 (μM) | Max % |
|---|---|---|---|---|
| 1 | 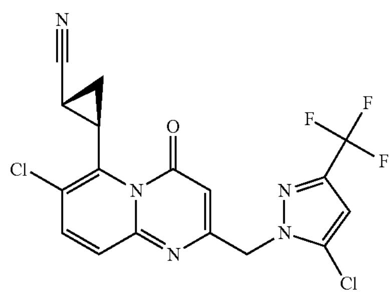 [SMILES: N#C[C@@H]1C[C@H]1c1c(Cl)ccc2nc(Cn3nc(C(F)(F)F)cc3Cl)cc(=O)n12] | (1R,2R)-2-[7-chloro-2-[[5-chloro-3-(trifluoromethyl)pyrazol-1-yl]methyl]-4-oxo-pyrido[1,2-a]pyrimidin-6-yl]cyclopropanecarbonitrile | 0.0368 | 135% |
| 2 | 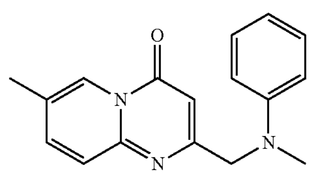 [SMILES: Cc1ccc2nc(CN(C)c3ccccc3)cc(=O)n2c1] | 7-methyl-2-[(N-methylanilino)methyl]pyrido[1,2-a]pyrimidin-4-one | | 75% |
| 3 | 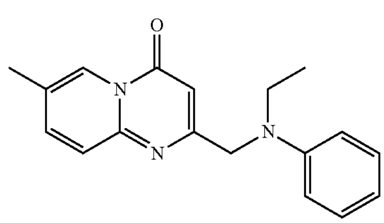 [SMILES: CCN(Cc1cc(=O)n2cc(C)ccc2n1)c1ccccc1] | 2-[(N-ethylanilino)methyl]-7-methyl-pyrido[1,2-a]pyrimidin-4-one | 11.1 | 122% |
| 4 | 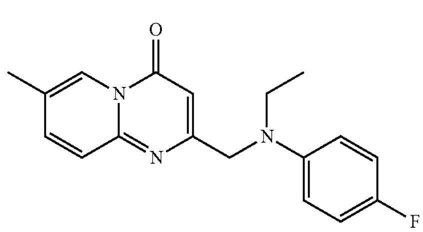 [SMILES: CCN(Cc1cc(=O)n2cc(C)ccc2n1)c1ccc(F)cc1] | 2-[(N-ethyl-4-fluoro-anilino)methyl]-7-methyl-pyrido[1,2-a]pyrimidin-4-one | 5.2 | 134% |

TABLE 1-continued

| | Structure | Name | EC50 (μM) | Max % |
|---|---|---|---|---|
| 5 | 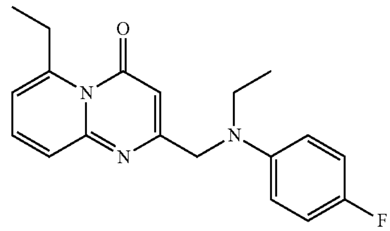 [SMILES: CCc1cccc2nc(CN(CC)c3ccc(F)cc3)cc(=O)n12] | 6-ethyl-2-[(N-ethyl-4-fluoro-anilino)methyl]pyrido[1,2-a]pyrimidin-4-one | 6.4 | 134% |
| 6 | 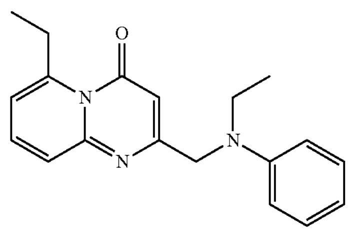 [SMILES: CCc1cccc2nc(CN(CC)c3ccccc3)cc(=O)n12] | 6-ethyl-2-[(N-ethylanilino)methyl]pyrido[1,2-a]pyrimidin-4-one | 11.5 | 138% |
| 7 | 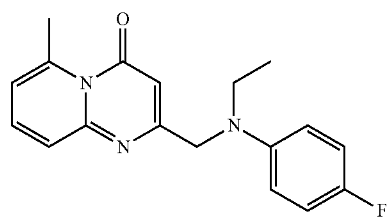 [SMILES: CCN(Cc1cc(=O)n2c(C)cccc2n1)c1ccc(F)cc1] | 2-[(N-ethyl-4-fluoro-anilino)methyl]-6-methyl-pyrido[1,2-a]pyrimidin-4-one | 13.6 | 111% |
| 8 | 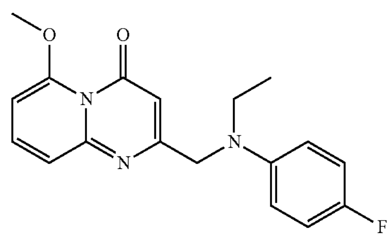 [SMILES: CCN(Cc1cc(=O)n2c(OC)cccc2n1)c1ccc(F)cc1] | 2-[(N-ethyl-fluoro-anilino)methyl]-6-methoxy-pyrido[1,2-a]pyrimidin-4-one | 4.4 | 117% |
| 9 | 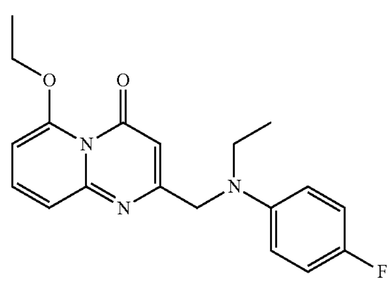 [SMILES: CCOc1cccc2nc(CN(CC)c3ccc(F)cc3)cc(=O)n12] | 6-ethoxy-2-[(N-ethyl-4-fluoro-anilino)methyl]pyrido[1,2-a]pyrimidin-4-one | 5.0 | 120% |
| 10 | 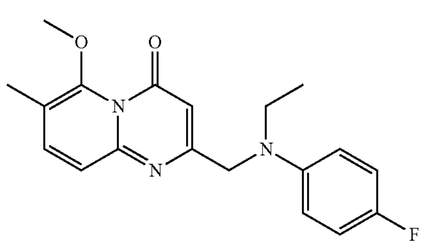 [SMILES: CCN(Cc1cc(=O)n2c(OC)c(C)ccc2n1)c1ccc(F)cc1] | 2-[(N-ethyl-4-fluoro-anilino)methyl]-6-methoxy-7-methyl-pyrido[1,2-a]pyrimidin-4-one | | 51% |

TABLE 1-continued

| | Structure | Name | EC50 (μM) | Max % |
|---|---|---|---|---|
| 11 | 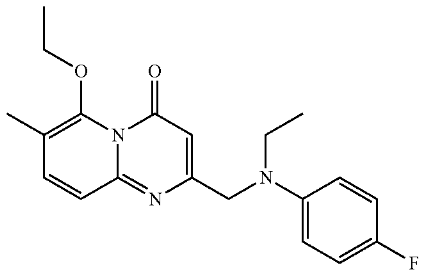 [SMILES: CCOc1c(C)ccc2nc(CN(CC)c3ccc(F)cc3)cc(=O)n12] | 6-ethoxy-2-[(N-ethyl-4-fluoro-anilino)methyl]-7-methyl-pyrido[1,2-a]pyrimidin-4-one | | 53% |
| 12 | 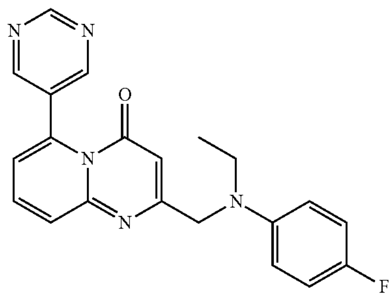 [SMILES: CCN(Cc1cc(=O)n2c(-c3cncnc3)cccc2n1)c1ccc(F)cc1] | 2-[(N-ethyl-4-fluoro-anilino)methyl]-6-pyrimidin-5-yl-pyrido[1,2-a]pyrimidin-4-one | 6.4 | 161% |
| 13 | 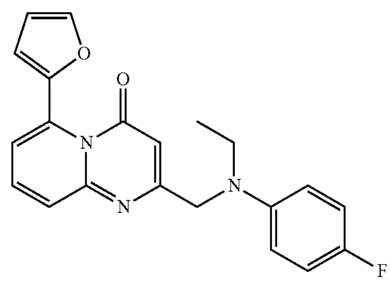 [SMILES: CCN(Cc1cc(=O)n2c(-c3ccco3)cccc2n1)c1ccc(F)cc1] | 2-[(N-ethyl-4-fluoro-anilino)methyl]-6-(2-furyl)pyrido[1,2-a]pyrimidin-4-one | 0.371 | 172% |
| 14 | 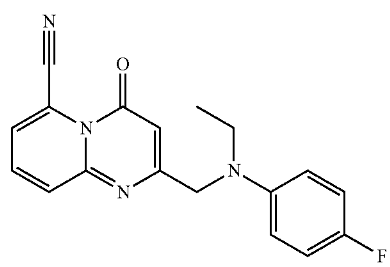 [SMILES: CCN(Cc1cc(=O)n2c(C#N)cccc2n1)c1ccc(F)cc1] | 2-[(N-ethyl-4-fluoro-anilino)methyl]-4-oxo-pyrido[1,2-a]pyrimidine-6-carbonitrile | 5.8 | 163% |
| 15 | 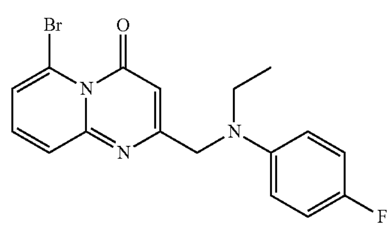 [SMILES: CCN(Cc1cc(=O)n2c(Br)cccc2n1)c1ccc(F)cc1] | 6-bromo-2-[(N-ethyl-4-fluoro-anilino)methyl]pyrido[1,2-a]pyrimidin-4-one | 6.2 | 159% |
| 16 | 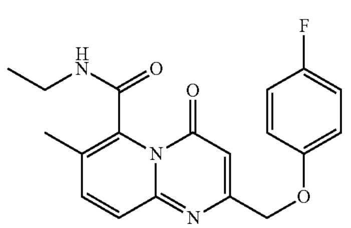 [SMILES: CCNC(=O)c1c(C)ccc2nc(COc3ccc(F)cc3)cc(=O)n12] | N-ethyl-2-[(4-fluorophenoxy)methyl]-7-methyl-4-oxo-pyrido[1,2-a]pyrimidine-6-carboxamide | 3.6 | 159% |

TABLE 1-continued

| | Structure | Name | EC50 (μM) | Max % |
|---|---|---|---|---|
| 17 | 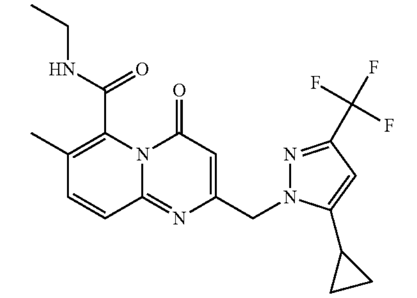 [SMILES: CCNC(=O)c1c(C)ccc2nc(Cn3nc(C(F)(F)F)cc3C3CC3)cc(=O)n12] | 2-[[5-cyclopropyl-3-(trifluoromethyl)pyrazol-1-yl]methyl]-N-ethyl-7-methyl-4-oxo-pyrido[1,2-a]pyrimidine-6-carboxamide | 4.0 | 148% |
| 18 | 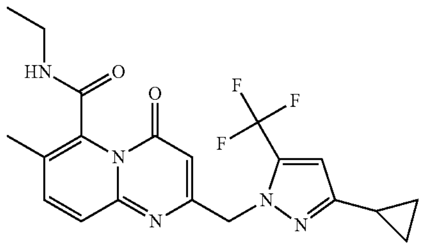 [SMILES: CCNC(=O)c1c(C)ccc2nc(Cn3nc(C4CC4)cc3C(F)(F)F)cc(=O)n12] | 2-[[3-cyclopropyl-5-(trifluoromethyl)pyrazol-1-yl]methyl]-N-ethyl-7-methyl-4-oxo-pyrido[1,2-a]pyrimidine-6-carboxamide | 16.2 | 122% |
| 19 | 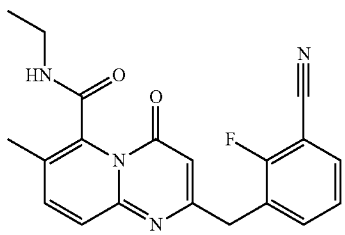 [SMILES: CCNC(=O)c1c(C)ccc2nc(Cc3cccc(C#N)c3F)cc(=O)n12] | 2-[(3-cyano-2-fluoro-phenyl)methyl]-N-ethyl-7-methyl-4-oxo-pyrido[1,2-a]pyrimidine-6-carboxamide | | 65% |
| 20 | 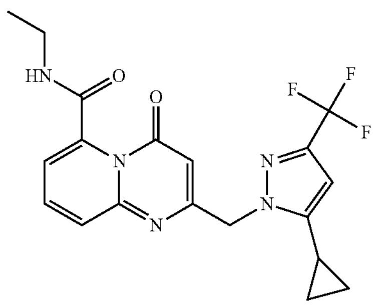 [SMILES: CCNC(=O)c1cccc2nc(Cn3nc(C(F)(F)F)cc3C3CC3)cc(=O)n12] | 2-[[5-cyclopropyl-3-(trifluoromethyl)pyrazol-1-yl]methyl]-N-ethyl-4-oxo-pyrido[1,2-a]pyrimidine-6-carboxamide | 7.4 | 116% |
| 21 | 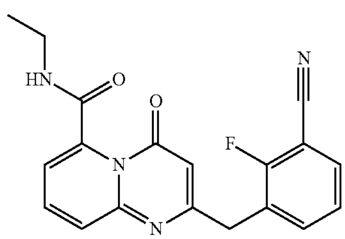 [SMILES: CCNC(=O)c1cccc2nc(Cc3cccc(C#N)c3F)cc(=O)n12] | 2-[(3-cyano-2-fluoro-phenyl)methyl]-N-ethyl-4-oxo-pyrido[1,2-a]pyrimidine-6-carboxamide | | 43% |
| 22 | 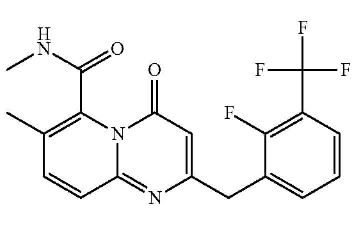 [SMILES: CNC(=O)c1c(C)ccc2nc(Cc3cccc(C(F)(F)F)c3F)cc(=O)n12] | 2-[[2-fluoro-3-(trifluoromethyl)phenyl]methyl]-N,7-dimethyl-4-oxo-pyrido[1,2-a]pyrimidine-6-carboxamide | | 69 |

TABLE 1-continued

| | Structure | Name | EC50 (μM) | Max % |
|---|---|---|---|---|
| 23 | 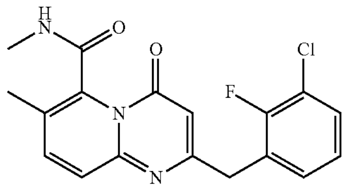 [SMILES: CNC(=O)c1c(C)ccc2nc(Cc3cccc(Cl)c3F)cc(=O)n12] | 2-[(3-chloro-2-fluoro-phenyl)methyl]-N,7-dimethyl-4-oxo-pyrido[1,2-a]pyrimidine-6-carboxamide | | 59 |
| 24 | 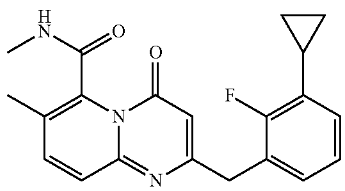 [SMILES: CNC(=O)c1c(C)ccc2nc(Cc3cccc(C4CC4)c3F)cc(=O)n12] | 2-[(3-cyclopropyl-2-fluoro-phenyl)methyl]-N,7-dimethyl-4-oxo-pyrido[1,2-a]pyrimidine-6-carboxamide | | 67% |
| 25 | 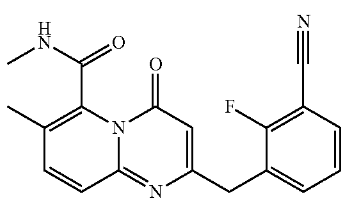 [SMILES: CNC(=O)c1c(C)ccc2nc(Cc3cccc(C#N)c3F)cc(=O)n12] | 2-[(3-cyano-2-fluoro-phenyl)methyl]-N,7-dimethyl-4-oxo-pyrido[1,2-a]pyrimidine-6-carboxamide | | 51% |
| 26 | 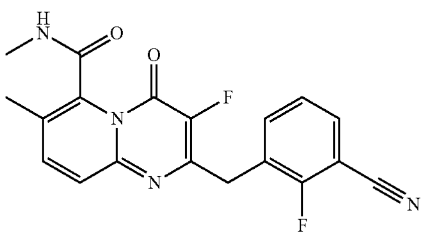 [SMILES: CNC(=O)c1c(C)ccc2nc(Cc3cccc(C#N)c3F)c(F)c(=O)n12] | 2-[(3-cyano-2-fluoro-phenyl)methyl]-3-fluoro-N,7-dimethyl-4-oxo-pyrido[1,2-a]pyrimidine-6-carboxamide | | 34% |
| 27 | 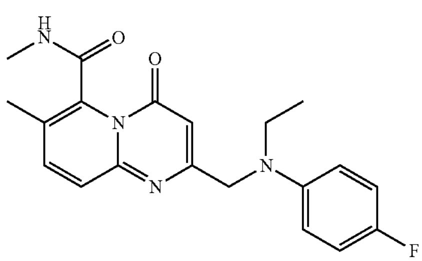 [SMILES: CCN(Cc1cc(=O)n2c(C(=O)NC)c(C)ccc2n1)c1ccc(F)cc1] | 2-[(N-ethyl-4-fluoro-anilino)methyl]-N,7-dimethyl-4-oxo-pyrido[1,2-a]pyrimidine-6-carboxamide | 2.7 | 162% |
| 28 | 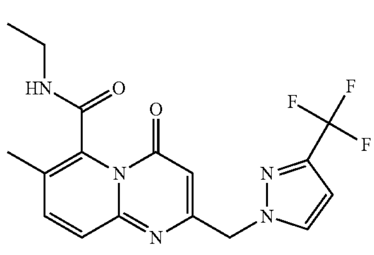 [SMILES: CCNC(=O)c1c(C)ccc2nc(Cn3ccc(C(F)(F)F)n3)cc(=O)n12] | N-ethyl-7-methyl-4-oxo-2-[[3-(trifluoromethyl)pyrazol-1-yl]methyl]pyrido[1,2-a]pyrimidine-6-carboxamide | | 60% |

TABLE 1-continued

| | Structure | Name | EC50 (µM) | Max % |
|---|---|---|---|---|
| 29 | 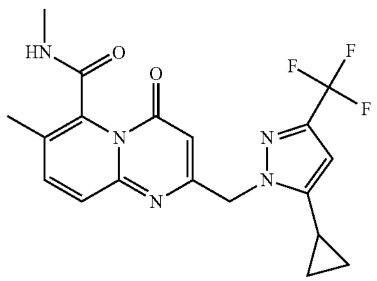 [SMILES: CNC(=O)c1c(C)ccc2nc(Cn3nc(C(F)(F)F)cc3C3CC3)cc(=O)n12] | 2-[[5-cyclopropyl-3-(trifluoromethyl)pyrazol-1-yl]methyl]-N,7-dimethyl-4-oxo-pyrido[1,2-a]pyrimidine-6-carboxamide | 5.9 | 147% |
| 30 | 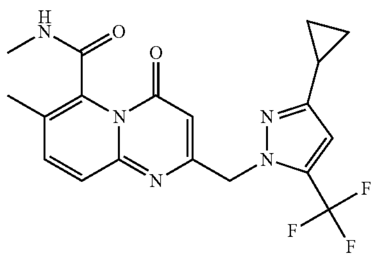 [SMILES: CNC(=O)c1c(C)ccc2nc(Cn3nc(C4CC4)cc3C(F)(F)F)cc(=O)n12] | 2-[[3-cyclopropyl-5-(trifluoromethyl)pyrazol-1-yl]methyl]-N,7-dimethyl-4-oxo-pyrido[1,2-a]pyrimidine-6-carboxamide | | 101% |
| 31 | 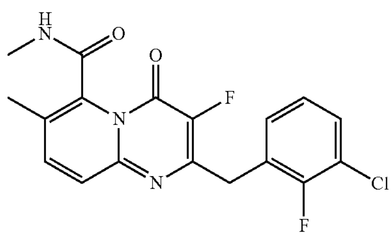 [SMILES: CNC(=O)c1c(C)ccc2nc(Cc3cccc(Cl)c3F)c(F)c(=O)n12] | 2-[(3-chloro-2-fluoro-phenyl)methyl]-3-fluoro-N,7-dimethyl-4-oxo-pyrido[1,2-a]pyrimidine-6-carboxamide | | 48% |
| 32 | 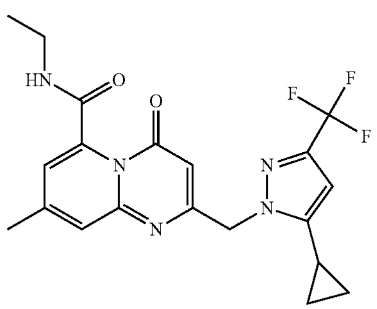 [SMILES: CCNC(=O)c1cc(C)cc2nc(Cn3nc(C(F)(F)F)cc3C3CC3)cc(=O)n12] | 2-[[5-cyclopropyl-3-(trifluoromethyl)pyrazol-1-yl]methyl-N-ethyl-8-methyl-4-oxo-pyrido[1,2-a]pyrimidine-6-carboxamide | | 136% |
| 33 | 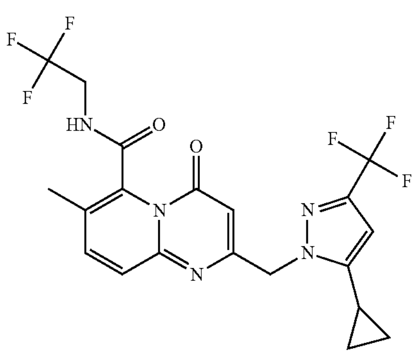 [SMILES: Cc1ccc2nc(Cn3nc(C(F)(F)F)cc3C3CC3)cc(=O)n2c1C(=O)NCC(F)(F)F] | 2-[[5-cyclopropyl-3-(trifluoromethyl)pyrazol-1-yl]methyl]-7-methyl-4-oxo-N-(2,2,2-trifluoroethyl)pyrido[1,2-a]pyrimidine-6-carboxamide | | 198% |

TABLE 1-continued

| | Structure | Name | EC50 (μM) | Max % |
|---|---|---|---|---|
| 34 | 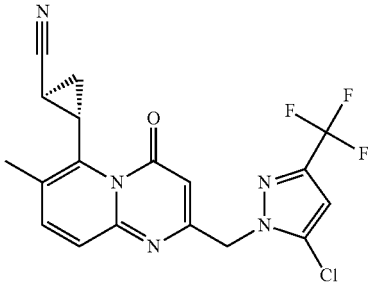 [SMILES: Cc1ccc2nc(Cn3nc(C(F)(F)F)cc3Cl)cc(=O)n2c1[C@H]1C[C@@H]1C#N] | (1S,2S)-2-[2-[[5-chloro-3-(trifluoromethyl)pyrazol-1-yl]methyl]-7-methyl-4-oxo-pyrido[1,2-a]pyrimidin-6-yl]cyclopropanecarbonitrile | 25.5 | 99% |
| 35 | 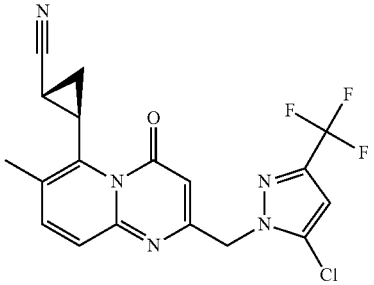 [SMILES: Cc1ccc2nc(Cn3nc(C(F)(F)F)cc3Cl)cc(=O)n2c1[C@@H]1C[C@H]1C#N] | (1R,2R)-2-[2-[[5-chloro-3-(trifluoromethyl)pyrazol-1-yl]methyl]-7-methyl-4-oxo-pyrido[1,2-a]pyrimidin-6-yl]cyclopropanecarbonitrile | 0.077 | 132% |
| 36 | 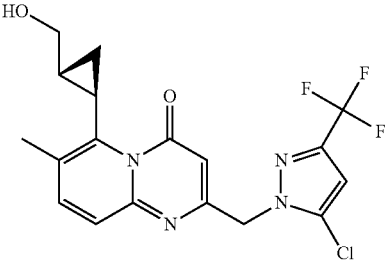 [SMILES: Cc1ccc2nc(Cn3nc(C(F)(F)F)cc3Cl)cc(=O)n2c1[C@@H]1C[C@H]1CO] | 2-[[5-chloro-3-(trifluoromethyl)pyrazol-1-yl]methyl]-6-[(1R,2R)-2-(hydroxymethyl)cyclopropyl]-7-methyl-pyrido[1,2-a]pyrimidin-4-one | 0.126 | 135% |
| 37 | 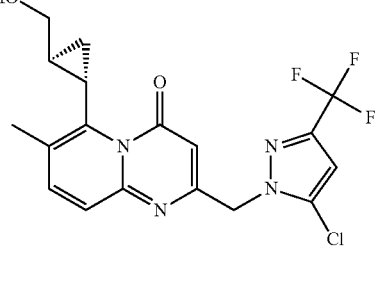 | 2-[[5-chloro-3-(trifluoromethyl)pyrazol-1-yl]methyl]-6-[(1S,2S)-2-(hydroxymethyl)cyclopropyl]-7-methyl-pyrido[1,2-a]pyrimidin-4-one | | 127% |
| 38 | 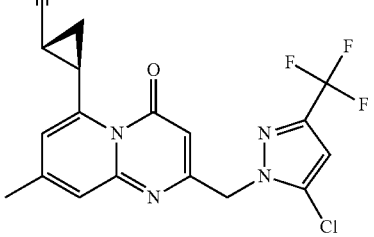 | (1R,2R)-2-(2-[[5-chloro-3-(trifluoromethyl)pyrazol-1-yl]methyl]-8-methyl-4-oxo-pyrido[1,2-a]pyrimidin-6-yl]cyclopropanecarbonitrile | 0.039 | 144% |

TABLE 1-continued

| | Structure | Name | EC50 (μM) | Max % |
|---|---|---|---|---|
| 39 | 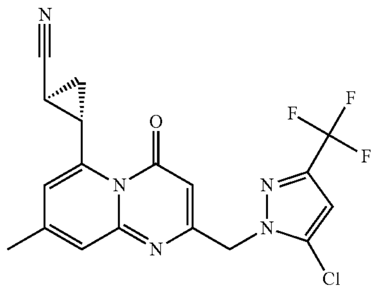 [SMILES: Cc1cc([C@H]2C[C@@H]2C#N)n2c(=O)cc(Cn3nc(C(F)(F)F)cc3Cl)nc2c1] | (1S,2S)-2-[2-[[5-chloro-3-(trifluoromethyl)pyrazol-1-yl]methyl]-8-methyl-4-oxo-pyrido[1,2-a]pyrimidin-6-yl]cyclopropanecarbonitrile | 0.951 | 120% |
| 40 | 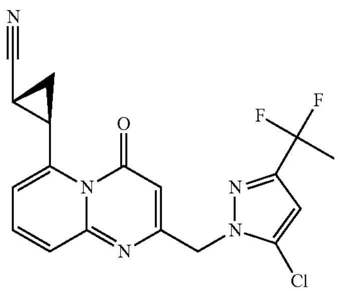 [SMILES: CC(F)(F)c1cc(Cl)n(Cc2cc(=O)n3c([C@@H]4C[C@H]4C#N)cccc3n2)n1] | (1R,2R)-2-[2-[[5-chloro-3-(trifluoromethyl)pyrazol-1-yl]methyl]-4-oxo-pyrido[1,2-a]pyrimidin-6-yl]cyclopropanecarbonitrile | 0.024 | 148% |
| 41 | 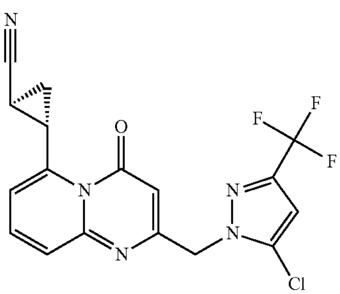 [SMILES: N#C[C@H]1C[C@@H]1c1cccc2nc(Cn3nc(C(F)(F)F)cc3Cl)cc(=O)n12] | (1S,2S)-2-[2-[[5-chloro-3-(trifluoromethyl)pyrazol-1-yl]methyl]-4-oxo-pyrido[1,2-a]pyrimidin-6-yl]cyclopropanecarbonitrile | 2.9 | 111% |
| 42 | 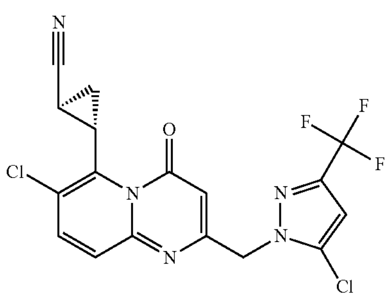 [SMILES: N#C[C@H]1C[C@@H]1c1c(Cl)ccc2nc(Cn3nc(C(F)(F)F)cc3Cl)cc(=O)n12] | (1S,2S)-2-[7-chloro-2-[[5-chloro-3-(trifluoromethyl)pyrazol-1-yl]methyl]-4-oxo-pyrido[1,2-a]pyrimidin-6-yl]cyclopropanecarbonitrile | 10.6 | 110% |
| 43 | 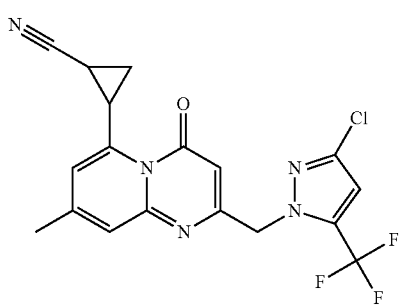 [SMILES: Cc1cc(C2CC2C#N)n2c(=O)cc(Cn3nc(Cl)cc3C(F)(F)F)nc2c1] | 2-[2-[[3-chloro-5-(trifluoromethyl)pyrazol-1-yl]methyl]-8-methyl-4-oxo-pyrido[1,2-a]pyrimidin-6-yl]cyclopropanecarbonitrile | 0.269 | 145% |

TABLE 1-continued

| | Structure | Name | EC50 (μM) | Max % |
|---|---|---|---|---|
| 44 | 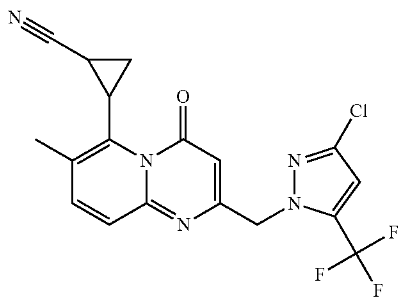 [SMILES: Cc1ccc2nc(Cn3nc(Cl)cc3C(F)(F)F)cc(=O)n2c1C1CC1C#N] | 2-[2-[[3-chloro-5-(trifluoromethyl)pyrazol-1-yl]methyl]-7-methyl-4-oxo-pyrido[1,2-a]pyrimidin-6-yl]cyclopropanecarbonitrile | 0.227 | 158% |
| 45 | 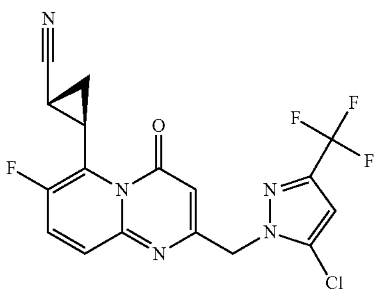 [SMILES: N#C[C@@H]1C[C@H]1c1c(F)ccc2nc(Cn3nc(C(F)(F)F)cc3Cl)cc(=O)n12] | (1R,2R)-2-[2-[[5-chloro-3-(trifluoromethyl)pyrazol-1-yl]methyl]-7-fluoro-4-oxo-pyrido[1,2-a]pyrimidin-6-yl]cyclopropanecarbonitrile | 0.021 | 151% |
| 46 | 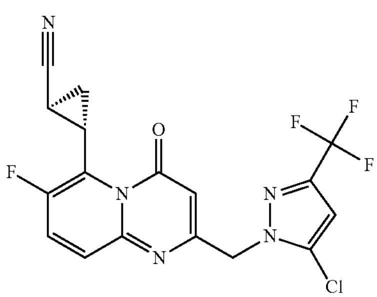 [SMILES: N#C[C@H]1C[C@@H]1c1c(F)ccc2nc(Cn3nc(C(F)(F)F)cc3Cl)cc(=O)n12] | (1S,2S)-2-[2-[[5-chloro-3-(trifluoromethyl)pyrazol-1-yl]methyl]-7-fluoro-4-oxo-pyrido[1,2-a]pyrimidin-6-yl]cyclopropanecarbonitrile | 3.22 | 107% |
| 47 | 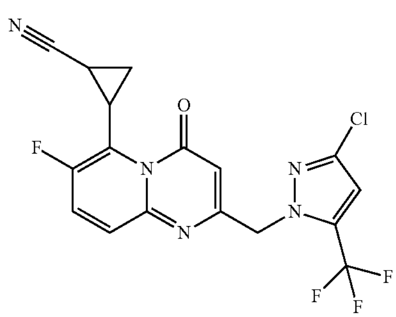 [SMILES: N#CC1CC1c1c(F)ccc2nc(Cn3nc(Cl)cc3C(F)(F)F)cc(=O)n12] | 2-[2-[[3-chloro-5-(trifluoromethyl)pyrazol-1-yl]methyl]-7-fluoro-4-oxo-pyrido[1,2-a]pyrimidin-6-yl]cyclopropanecarbonitrile | 0.178 | 200% |
| 48 | 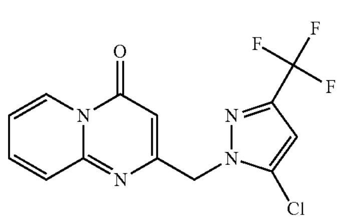 [SMILES: O=c1cc(Cn2nc(C(F)(F)F)cc2Cl)nc2ccccn12] | 2-[[5-chloro-3-(trifluoromethyl)pyrazol-1-yl]methyl]pyrido[1,2-a]pyrimidin-4-one | 32.4 | 73% |

TABLE 1-continued

| | Structure | Name | EC50 (μM) | Max % |
|---|---|---|---|---|
| 49 | 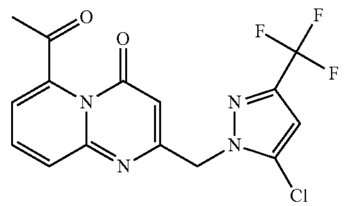 [SMILES: CC(=O)c1cccc2nc(Cn3nc(C(F)(F)F)cc3Cl)cc(=O)n12] | 6-acetyl-2-[[5-chloro-3-(trifluoromethyl)pyrazol-1-yl]methyl]pyrido[1,2-a]pyrimidin-4-one | 12.3 | 126% |
| 50 | 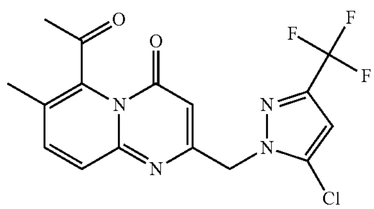 [SMILES: CC(=O)c1c(C)ccc2nc(Cn3nc(C(F)(F)F)cc3Cl)cc(=O)n12] | 6-acetyl-2-[[5-chloro-3-(trifluoromethyl)pyrazol-1-yl]methyl]-7-methyl-pyrido[1,2-a]pyrimidin-4-one | 7.7 | 124 |
| 51 | 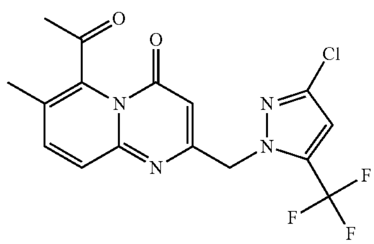 [SMILES: CC(=O)c1c(C)ccc2nc(Cn3nc(Cl)cc3C(F)(F)F)cc(=O)n12] | 6-acetyl-2-[[3-chloro-5-(trifluoromethyl)pyrazol-1-yl]methyl]-7-methyl-pyrido[1,2-a]pyrimidin-4-one | 9.1 | 114% |
| 52 | 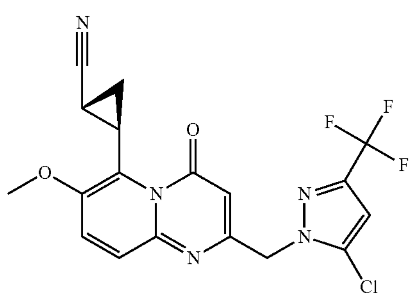 [SMILES: COc1ccc2nc(Cn3nc(C(F)(F)F)cc3Cl)cc(=O)n2c1[C@@H]1C[C@H]1C#N] | (1R,2R)-2-[2-[[5-chloro-3-(trifluoromethyl)pyrazol-1-yl]methyl]-7-methoxy-4-oxo-pyrido[1,2-a]pyrimidin-6-yl]cyclopropanecarbonitrile | 0.079 | 120% |
| 53 | 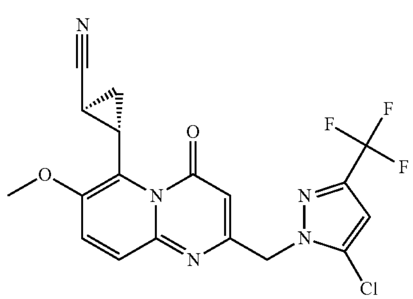 [SMILES: COc1ccc2nc(Cn3nc(C(F)(F)F)cc3Cl)cc(=O)n2c1[C@H]1C[C@@H]1C#N] | (1S,2S)-2-[2-[[5-chloro-3-(trifluoromethyl)pyrazol-1-yl]methyl]-7-methoxy-4-oxo-pyrido[1,2-a]pyrimidin-6-yl]cyclopropanecarbonitrile | | 100% |
| 54 | 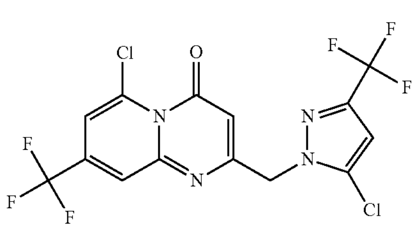 [SMILES: O=c1cc(Cn2nc(C(F)(F)F)cc2Cl)nc2cc(C(F)(F)F)cc(Cl)n12] | 6-chloro-2-[[5-chloro-3-(trifluoromethyl)pyrazol-1-yl]methyl]-8-(trifluoromethyl)pyrido[1,2-a]pyrimidin-4-one | 24.7 | 150% |

TABLE 1-continued

| | Structure | Name | EC50 (µM) | Max % |
|---|---|---|---|---|
| 55 | 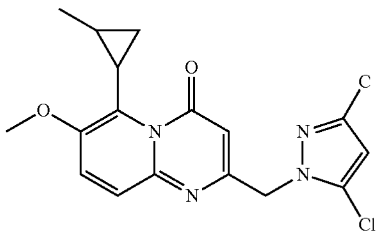 [SMILES: COc1ccc2nc(Cn3nc(C)cc3Cl)cc(=O)n2c1C1CC1C] | 2-((3,5-dichloro-1H-pyrazol-1-yl)methyl)-7-methoxy-6-(2-methylcyclopropyl)-4H-pyrido[1,2-a]pyrimidin-4-one | 0.102 | 116% |
| 56 | 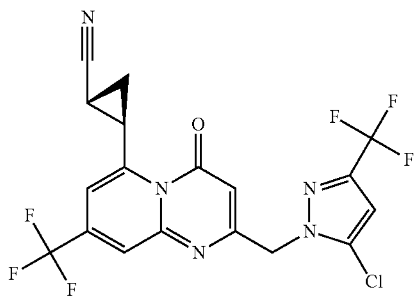 [SMILES: N#C[C@@H]1C[C@H]1c1cc(C(F)(F)F)cc2nc(Cn3nc(C(F)(F)F)cc3Cl)cc(=O)n12] | (1R,2R)-2-(2-((5-chloro-3-(trifluoromethyl)-1H-pyrazol-1-yl)methyl)-4-oxo-8-(trifluoromethyl)-4H-pyrido[1,2-a]pyrimidin-6-yl)cyclopropanecarbonitrile | 0.123 | 142% |
| 57 | | (1R,2R)-2-(2-((3,5-dichloro-1H-pyrazol-1-yl)methyl)-8-methyl-4-oxo-4H-pyrido[1,2-a]pyrimidin-6-yl)cyclopropanecarbonitrile | 0.222 | 154% |

Proton NMR and LCMS data for selected compounds of Table 1 are provided below, with the compound numbers below corresponding to the compound numbering in Table 1:

Compound 45, (1R,2R)-2-(2-((5-chloro-3-(trifluoromethyl)-1H-pyrazol-1-yl)methyl)-7-methyl-4-oxo-4H-pyrido[1,2-a]pyrimidin-6-yl)cyclopropanecarbonitrile: LCMS, m/z=408 [M+H]$^+$. $^1$HNMR (300 MHz, CDCl$_3$) δ 7.45-7.36 (m, 2H), 6.61 (s, 1H), 5.80 (s, 1H), 5.36 (s, 2H), 3.36-3.34 (m, 1H), 2.43 (s, 3H), 1.81-1.75 (m, 1H), 1.41-1.35 (m, 1H), 1.13-1.06 (m, 1H)

Compound 69, (1R,2R)-2-[2-[[5-chloro-3-(trifluoromethyl)pyrazol-1-yl]methyl]-7-methoxy-4-oxo-pyrido[1,2-a]pyrimidin-6-yl]cyclopropanecarbonitrile: LCMS (ESI): M+H$^+$=424.0; $^1$HNMR (300 MHz, CDCl$_3$) δ 7.90 (d, J=4.5 Hz, 1H), 7.71 (d, J=4.5 Hz, 1H), 6.62 (s, 1H), 5.74 (s, 1H), 5.43 (s, 2H), 4.06 (s, 3H), 3.29-3.21 (m, 1H), 1.88-1.72 (m, 1H), 1.50-1.41 (m, 1H), 1.18-1.09 (m, 1H)

Compound 73, 2-((3,5-dichloro-1H-pyrazol-1-yl)methyl)-7-methoxy-6-(2-methylcyclopropyl)-4H-pyrido[1,2-a]pyrimidin-4-one: LCMS (ESI): M+H$^+$=379.1. $^1$H NMR (400 MHz, CDCl$_3$) δ 7.49 (d, J=9.6 Hz, 1H), 7.41 (bs, 1H), 6.27 (s, 1H), 5.76 (s, 1H), 5.25 (s, 2H), 3.97 (s, 3H), 2.27-2.22 (m, 1H), 1.20 (d, J=6.0 Hz, 3H), 0.84-0.73 (m, 2H), 0.62-0.59 (m, 1H).

Compound 74, (1R,2R)-2-(2-((5-chloro-3-(trifluoromethyl)-1H-pyrazol-1-yl)methyl)-4-oxo-8-(trifluoromethyl)-4H-pyrido[1,2-a]pyrimidin-6-yl)cyclopropanecarbonitrile: LCMS (ESI): M+H$^+$=462.0; $^1$HNMR (400 MHz, CDCl3) δ 7.64 (s, 1H), 6.79 (s, 1H), 6.62 (s, 1H), 5.97 (s, 1H), 5.35 (s, 2H), 3.86-3.81 (m, 1H), 1.83-1.72 (m, 2H), 1.54-1.50 (m, 1H).

Compound 75, (1R,2R)-2-(2-((3,5-dichloro-1H-pyrazol-1-yl)methyl)-8-methyl-4-oxo-4H-pyrido[1,2-a]pyrimidin-6-yl)cyclopropanecarbonitrile: LCMS (ESI): M+H$^+$=374.0; $^1$HNMR (400 MHz, CDCl3) δ 7.37 (s, 1H), 6.69 (s, 1H), 6.30 (s, 1H), 5.78 (s, 1H), 5.28 (s, 2H), 3.88-3.82 (m, 1H), 2.40 (s, 3H), 1.79-1.69 (m, 2H), 1.49-1.44 (m, 1H).

Assay 1: Cell-Based Assay

HEK cells stably transfected with tetracycline inducible hNR1 and hNR2A were seeded into clear bottom 384 well poly-D-lysine coated plates (2.5×10$^4$ cells per well) in Minimum Essential Media (MEM; without L-) including 7.5 µg mL doxycycline and 500 µM (+)-ketamine. The cells were incubated at 37° C. in 5% CO$_2$ for 24 h. For measurement of changes in cytosolic calcium, the seeding media was removed and the cells incubated at 37° C. for 60 min with 1× Becton Dickinson Calcium Assay Kit reagent in Hanks Balanced Salt Solution (HBSS; w/o magnesium, including 1.8 mM calcium, 0.65 mg ml$^{-1}$ probenecid and 10 µM (+)-ketamine, pH 7.15) then allowed to equilibrate to rt for 30 min. Concentration-effect curves to Positive Allosteric Modulators (PAMs) were constructed by adding different concentrations (with 30 µM glycine and 300 nM L-glutamate (EC$_{30}$)) to different wells in HBSS. Compounds were added after a 10 second baseline read and maximum level of relative fluorescence units (RFU) was measured over a 5 min period. Responses were scaled relative to 100 µM L-glutamate maximal response (100%) and 0 µM L-glutamate (0%). EC$_{50}$ values are provided for compounds reaching maximal response plateaus, and the max % (EC$_{50}$ (--)) only if no plateau was reached.

A four-parameter Hill equation was fitted to individual concentration-effect curves:

$$Y = S_0 + \frac{S_{int} - S_0}{1 + \left(\frac{10^{logAC50}}{10^c}\right)^n}$$

in which Y, $S_0$, $S_{inf}$, $AC_{50}$, n and c were effect, lower-asymptote, upper-asymptote, mid-point location, slope parameter, and concentration respectively.

Data for compounds tested in this assay are shown above in Table 1.

While the present invention has been described in conjunction with the specific embodiments set forth above, many alternatives, modifications and other variations thereof will be apparent to those of ordinary skill in the art. All such alternatives, modifications and variations are intended to fall within the spirit and scope of the present invention.

The invention claimed is:

1. A compound of Formula I

I or a pharmaceutically acceptable salt thereof, wherein:
X is: —O—Ar; —NR$^a$—Ar; or —Ar;
R$^1$ is: hydrogen; C$_{1-6}$ alkyl; halo; C$_{1-6}$ alkoxy; cyano; heteroaryl selected from furanyl, thienyl, pyrrolyl, pyrazolyl, imidazolyl, pyridinyl and pyrimidinyl, each of which may be unsubstituted or substituted once or twice with R$^b$; —C(O)—NHR$^c$; —C(O)—R$^c$; or cyclopropyl which may be unsubstituted or substituted once or twice with R$^d$;
R$^2$ is: hydrogen; C$_{1-6}$ alkyl; C$_{1-6}$ alkoxy; halo; or halo-C$_{1-6}$ alkyl;
R$^3$ is: hydrogen; C$_{1-6}$ alkyl; C$_{1-6}$ alkoxy; halo; or halo-C$_{1-6}$ alkyl;
R$^4$ is: hydrogen; or C$_{1-6}$ alkyl;
R$^5$ is: hydrogen; or C$_{1-6}$ alkyl;
R$^6$ is: hydrogen; or C$_{1-6}$ alkyl;
Ar is: phenyl or pyrazolyl, each of which may be unsubstituted or substituted one or two times with R$^e$;
R$^a$ is: hydrogen; or C$_{1-6}$ alkyl;
each R$^b$ is independently: C$_{1-6}$ alkyl; halo; halo-C$_{1-6}$ alkyl; or cyclopropyl;
R$^c$ is: C$_{1-6}$alkyl; or halo-C$_{1-6}$alkyl;
R$^d$ is: C$_{1-6}$alkyl; halo; halo-C$_{1-6}$alkyl; hydroxy-C$_{1-6}$alkyl; C$_{1-6}$alkoxy-C$_{1-6}$alkyl; or cyano;
each R$^e$ is independently: C$_{1-6}$ alkyl; halo; halo-C$_{1-6}$ alkyl; —NH—C(O)—R$^f$; cyano; or cyclopropyl; and
R$^f$ is furanyl, thienyl, pyrrolyl, pyrazolyl or imidazolyl;
provided that 2-Benzyl-6-methyl-pyrido[1,2-a]pyrimidin-4-one; and 2-Benzyl-pyrido[1,2-a]pyrimidin-4-one; are excluded.

2. The compound of claim 1, wherein X is Ar, or a pharmaceutically acceptable salt thereof.

3. The compound of claim 1, wherein R$^1$ is: C$_{1-6}$ alkyl; halo; C$_{1-6}$ alkoxy; cyano; or cyclopropyl which may be unsubstituted or substituted once or twice with R$^d$, or a pharmaceutically acceptable salt thereof.

4. The compound of claim 1, wherein R$^1$ is cyclopropyl which may be unsubstituted or substituted once or twice with R$^d$, or a pharmaceutically acceptable salt thereof.

5. The compound of claim 1, wherein R$^2$ is hydrogen, halo or C$_{1-6}$ alkyl, or a pharmaceutically acceptable salt thereof.

6. The compound of claim 1, wherein R$^3$ is hydrogen, C$_{1-6}$ alkyl or halo-C$_{1-6}$alkyl, or a pharmaceutically acceptable salt thereof.

7. The compound of claim 1, wherein R$^4$ is hydrogen, or a pharmaceutically acceptable salt thereof.

8. The compound of claim 1, wherein R$^5$ is hydrogen, or a pharmaceutically acceptable salt thereof.

9. The compound of claim 1, wherein R$^6$ is hydrogen, or a pharmaceutically acceptable salt thereof.

10. The compound of claim 1, wherein Ar is pyrazolyl substituted one or two times with R$^e$, or a pharmaceutically acceptable salt thereof.

11. The compound of claim 1, wherein Ar is 3-chloro-5-(trifluoromethyl)pyrazol-1-yl, or a pharmaceutically acceptable salt thereof.

12. The compound of claim 1, wherein each R$^d$ is independently cyano, C$_{1-6}$alkyl or hydroxy-C$_{1-6}$ alkyl, or a pharmaceutically acceptable salt thereof.

13. The compound of claim 1, wherein R$^d$ is cyano, or a pharmaceutically acceptable salt thereof.

14. The compound of claim 1, wherein each R$^e$ is independently halo or halo-C$_{1-6}$ alkyl, or a pharmaceutically acceptable salt thereof.

15. The compound of claim 1, wherein said compound is of formula III

III or a pharmaceutically acceptable salt thereof.

16. The compound of claim 1, wherein said compound is of formula IV

IV or a pharmaceutically acceptable salt thereof.

17. The compound of claim 1, wherein said compound is of formula V

V or a pharmaceutically acceptable salt thereof.

18. The compound of claim 17, wherein $R^d$ is cyano, $C_{1-6}$alkyl or hydroxy-$C_{1-6}$alkyl, or a pharmaceutically acceptable salt thereof.

19. The compound of claim 17, wherein each $R^e$ is independently halo or halo-$C_{1-6}$ alkyl, or a pharmaceutically acceptable salt thereof.

20. The compound of claim 1 selected from
(1R,2R)-2-[7-chloro-2-[[5-chloro-3-(trifluoromethyl)pyrazol-1-yl]methyl]-4-oxo-pyrido[1,2-a]pyrimidin-6-yl]cyclopropanecarbonitrile;
7-methyl-2-[(N-methylanilino)methyl]pyrido[1,2-a]pyrimidin-4-one;
2-[(N-ethylanilino)methyl]-7-methyl-pyrido[1,2-a]pyrimidin-4-one;
2-[(N-ethyl-4-fluoro-anilino)methyl]-7-methyl-pyrido[1,2-a]pyrimidin-4-one;
6-ethyl-2-[(N-ethyl-4-fluoro-anilino)methyl]pyrido[1,2-a]pyrimidin-4-one;
6-ethyl-2-[(N-ethylanilino)methyl]pyrido[1,2-a]pyrimidin-4-one;
2-[(N-ethyl-4-fluoro-anilino)methyl]-6-methyl-pyrido[1,2-a]pyrimidin-4-one;
2-[(N-ethyl-4-fluoro-anilino)methyl]-6-methoxy-pyrido[1,2-a]pyrimidin-4-one;
6-ethoxy-2-[(N-ethyl-4-fluoro-anilino)methyl]pyrido[1,2-a]pyrimidin-4-one;
2-[(N-ethyl-4-fluoro-anilino)methyl]-6-methoxy-7-methyl-pyrido[1,2-a]pyrimidin-4-one;
6-ethoxy-2-[(N-ethyl-4-fluoro-anilino)methyl]-7-methyl-pyrido[1,2-a]pyrimidin-4-one;
2-[(N-ethyl-4-fluoro-anilino)methyl]-6-pyrimidin-5-yl-pyrido[1,2-a]pyrimidin-4-one;
2-[(N-ethyl-4-fluoro-anilino)methyl]-6-(2-furyl)pyrido[1,2-a]pyrimidin-4-one;
2-[(N-ethyl-4-fluoro-anilino)methyl]-4-oxo-pyrido[1,2-a]pyrimidine-6-carbonitrile;
6-bromo-2-[(N-ethyl-4-fluoro-anilino)methyl]pyrido[1,2-a]pyrimidin-4-one;
N-ethyl-2-[(4-fluorophenoxy)methyl]-7-methyl-4-oxo-pyrido[1,2-a]pyrimidine-6-carboxamide;
2-[[5-cyclopropyl-3-(trifluoromethyl)pyrazol-1-yl]methyl]-N-ethyl-7-methyl-4-oxo-pyrido[1,2-a]pyrimidine-6-carboxamide;
2-[[3-cyclopropyl-5-(trifluoromethyl)pyrazol-1-yl]methyl]-N-ethyl-7-methyl-4-oxo-pyrido[1,2-a]pyrimidine-6-carboxamide;
2-[(3-cyano-2-fluoro-phenyl)methyl]-N-ethyl-7-methyl-4-oxo-pyrido[1,2-a]pyrimidine-6-carboxamide;
2-[[5-cyclopropyl-3-(trifluoromethyl)pyrazol-1-yl]methyl]-N-ethyl-4-oxo-pyrido[1,2-a]pyrimidine-6-carboxamide;
2-[(3-cyano-2-fluoro-phenyl)methyl]-N-ethyl-4-oxo-pyrido[1,2-a]pyrimidine-6-carboxamide;
2-[[2-fluoro-3-(trifluoromethyl)phenyl]methyl]-N,7-dimethyl-4-oxo-pyrido[1,2-a]pyrimidine-6-carboxamide;
2-[(3-chloro-2-fluoro-phenyl)methyl]-N,7-dimethyl-4-oxo-pyrido[1,2-a]pyrimidine-6-carboxamide;
2-[(3-cyclopropyl-2-fluoro-phenyl)methyl]-N,7-dimethyl-4-oxo-pyrido[1,2-a]pyrimidine-6-carboxamide;
2-[(3-cyano-2-fluoro-phenyl)methyl]-N,7-dimethyl-4-oxo-pyrido[1,2-a]pyrimidine-6-carboxamide;
2-[(3-cyano-2-fluoro-phenyl)methyl]-3-fluoro-N,7-dimethyl-4-oxo-pyrido[1,2-a]pyrimidine-6-carboxamide;
2-[(N-ethyl-4-fluoro-anilino)methyl]-N,7-dimethyl-4-oxo-pyrido[1,2-a]pyrimidine-6-carboxamide;
N-ethyl-7-methyl-4-oxo-2-[[3-(trifluoromethyl)pyrazol-1-yl]methyl]pyrido[1,2-a]pyrimidine-6-carboxamide;
2-[[5-cyclopropyl-3-(trifluoromethyl)pyrazol-1-yl]methyl]-N,7-dimethyl-4-oxo-pyrido[1,2-a]pyrimidine-6-carboxamide;
2-[[3-cyclopropyl-5-(trifluoromethyl)pyrazol-1-yl]methyl]-N,7-dimethyl-4-oxo-pyrido[1,2-a]pyrimidine-6-carboxamide;
2-[(3-chloro-2-fluoro-phenyl)methyl]-3-fluoro-N,7-dimethyl-4-oxo-pyrido[1,2-a]pyrimidine-6-carboxamide;
2-[[5-cyclopropyl-3-(trifluoromethyl)pyrazol-1-yl]methyl]-N-ethyl-8-methyl-4-oxo-pyrido[1,2-a]pyrimidine-6-carboxamide;
2-[[5-cyclopropyl-3-(trifluoromethyl)pyrazol-1-yl]methyl]-7-methyl-4-oxo-N-(2,2,2-trifluoroethyl)pyrido[1,2-a]pyrimidine-6-carboxamide;
(1S,2S)-2-[2-[[5-chloro-3-(trifluoromethyl)pyrazol-1-yl]methyl]-7-methyl-4-oxo-pyrido[1,2-a]pyrimidin-6-yl]cyclopropanecarbonitrile;
(1R,2R)-2-[2-[[5-chloro-3-(trifluoromethyl)pyrazol-1-yl]methyl]-7-methyl-4-oxo-pyrido[1,2-a]pyrimidin-6-yl]cyclopropanecarbonitrile;
2-[[5-chloro-3-(trifluoromethyl)pyrazol-1-yl]methyl]-6-[(1R,2R)-2-(hydroxymethyl)cyclopropyl]-7-methyl-pyrido[1,2-a]pyrimidin-4-one;
2-[[5-chloro-3-(trifluoromethyl)pyrazol-1-yl]methyl]-6-[(1S,2S)-2-(hydroxymethyl)cyclopropyl]-7-methyl-pyrido[1,2-a]pyrimidin-4-one;
(1R,2R)-2-[2-[[5-chloro-3-(trifluoromethyl)pyrazol-1-yl]methyl]-8-methyl-4-oxo-pyrido[1,2-a]pyrimidin-6-yl]cyclopropanecarbonitrile;
(1S,2S)-2-2-[[5-chloro-3-(trifluoromethyl)pyrazol-1-yl]methyl]-8-methyl-4-oxo-pyrido[1,2-a]pyrimidin-6-yl]cyclopropanecarbonitrile;
(1R,2R)-2-[2-[[5-chloro-3-(trifluoromethyl)pyrazol-1-yl]methyl]-4-oxo-pyrido[1,2-a]pyrimidin-6-yl]cyclopropanecarbonitrile;
(1S,2S)-2-[2-[[5-chloro-3-(trifluoromethyl)pyrazol-1-yl]methyl]-4-oxo-pyrido[1,2-a]pyrimidin-6-yl]cyclopropanecarbonitrile;
(1S,2S)-2-[7-chloro-2-[[5-chloro-3-(trifluoromethyl)pyrazol-1-yl]methyl]-4-oxo-pyrido[1,2-a]pyrimidin-6-yl]cyclopropanecarbonitrile;
2-[2-[[3-chloro-5-(trifluoromethyl)pyrazol-1-yl]methyl]-8-methyl-4-oxo-pyrido[1,2-a]pyrimidin-6-yl]cyclopropanecarbonitrile;
2-[2-[[3-chloro-5-(trifluoromethyl)pyrazol-1-yl]methyl]-7-methyl-4-oxo-pyrido[1,2-a]pyrimidin-6-yl]cyclopropanecarbonitrile;
(1R,2R)-2-[2-[[5-chloro-3-(trifluoromethyl)pyrazol-1-yl]methyl]-7-fluoro-4-oxo-pyrido[1,2-a]pyrimidin-6-yl]cyclopropanecarbonitrile;
(1S,2S)-2-[2-[[5-chloro-3-(trifluoromethyl)pyrazol-1-yl]methyl]-7-fluoro-4-oxo-pyrido[1,2-a]pyrimidin-6-yl]cyclopropanecarbonitrile;
2-[2-[[3-chloro-5-(trifluoromethyl)pyrazol-1-yl]methyl]-7-fluoro-4-oxo-pyrido[1,2-a]pyrimidin-6-yl]cyclopropanecarbonitrile;
2-[[5-chloro-3-(trifluoromethyl)pyrazol-1-yl]methyl]pyrido[1,2-a]pyrimidin-4-one;
6-acetyl-2-[[5-chloro-3-(trifluoromethyl)pyrazol-1-yl]methyl]pyrido[1,2-a]pyrimidin-4-one;
6-acetyl-2-[[5-chloro-3-(trifluoromethyl)pyrazol-1-yl]methyl]-7-methyl-pyrido[1,2-a]pyrimidin-4-one;
6-acetyl-2-[[3-chloro-5-(trifluoromethyl)pyrazol-1-yl]methyl]-7-methyl-pyrido[1,2-a]pyrimidin-4-one;

(1R,2R)-2-[2-[[5-chloro-3-(trifluoromethyl)pyrazol-1-yl]methyl]-7-methoxy-4-oxo-pyrido[1,2-a]pyrimidin-6-yl]cyclopropanecarbonitrile;

(1S,2S)-2-[2-[[5-chloro-3-(trifluoromethyl)pyrazol-1-yl]methyl]-7-methoxy-4-oxo-pyrido[1,2-a]pyrimidin-6-yl]cyclopropanecarbonitrile;

6-chloro-2-[[5-chloro-3-(trifluoromethyl)pyrazol-1-yl]methyl]-8-(trifluoromethyl)pyrido[1,2-a]pyrimidin-4-one;

2-((3,5-dichloro-1H-pyrazol-1-yl)methyl)-7-methoxy-6-(2-methylcyclopropyl)-4H-pyrido[1,2-a]pyrimidin-4-one;

(1R,2R)-2-(2-((5-chloro-3-(trifluoromethyl)-1H-pyrazol-1-yl)methyl)-4-oxo-8-(trifluoromethyl)-4H-pyrido[1,2-a]pyrimidin-6-yl)cyclopropanecarbonitrile; and (1R,2R)-2-(2-((3,5-dichloro-1H-pyrazol-1-yl)methyl)-8-methyl-4-oxo-4H-pyrido[1,2-a]pyrimidin-6-yl)cyclopropanecarbonitrile;

or a pharmaceutically acceptable salt thereof.

21. A compound that is (1R,2R)-2-[7-chloro-2-[[5-chloro-3-(trifluoromethyl)pyrazol-1-yl]methyl]-4-oxo-pyrido[1,2-a]pyrimidin-6-yl]cyclopropanecarbonitrile, or a pharmaceutically acceptable salt thereof.

22. A compound that is (1R,2R)-2-[2-[[5-chloro-3-(trifluoromethyl)pyrazol-1-yl]methyl]-7-methyl-4-oxo-pyrido[1,2-a]pyrimidin-6-yl]cyclopropanecarbonitrile, or a pharmaceutically acceptable salt thereof.

23. A compound that is (1R,2R)-2-[2-[[5-chloro-3-(trifluoromethyl)pyrazol-1-yl]methyl]-8-methyl-4-oxo-pyrido[1,2-a]pyrimidin-6-yl]cyclopropanecarbonitrile, or a pharmaceutically acceptable salt thereof.

24. A compound that is (1R,2R)-2-[2-[[5-chloro-3-(trifluoromethyl)pyrazol-1-yl]methyl]-4-oxo-pyrido[1,2-a]pyrimidin-6-yl]cyclopropanecarbonitrile, or a pharmaceutically acceptable salt thereof.

25. A compound that is (1R,2R)-2-[2-[[5-chloro-3-(trifluoromethyl)pyrazol-1-yl]methyl]-7-fluoro-4-oxo-pyrido[1,2-a]pyrimidin-6-yl]cyclopropanecarbonitrile, or a pharmaceutically acceptable salt thereof.

26. A compound that is (1R,2R)-2-[2-[[5-chloro-3-(trifluoromethyl)pyrazol-1-yl]methyl]-7-methoxy-4-oxo-pyrido[1,2-a]pyrimidin-6-yl]cyclopropanecarbonitrile, or a pharmaceutically acceptable salt thereof.

27. A compound that is (1R,2R)-2-(2-((5-chloro-3-(trifluoromethyl)-1H-pyrazol-1-yl)methyl)-4-oxo-8-(trifluoromethyl)-4H-pyrido[1,2-a]pyrimidin-6-yl)cyclopropanecarbonitrile, or a pharmaceutically acceptable salt thereof.

28. A pharmaceutical composition comprising: (a) an effective amount of at least one compound of claim 1, or a pharmaceutically acceptable salt thereof, and (b) a pharmaceutically acceptable carrier.

* * * * *